(12) United States Patent
Zemla et al.

(10) Patent No.: US 8,452,542 B2
(45) Date of Patent: May 28, 2013

(54) STRUCTURE-SEQUENCE BASED ANALYSIS FOR IDENTIFICATION OF CONSERVED REGIONS IN PROTEINS

(75) Inventors: Adam T. Zemla, Brentwood, CA (US); Carol E. Zhou, Pleasanton, CA (US); Marisa W. Lam, Pleasanton, CA (US); Jason R. Smith, Mountain House, CA (US); Elizabeth Pardes, Pleasanton, CA (US)

(73) Assignee: Lawrence Livermore National Security, LLC., Livermore, CA (US)

(*) Notice: Subject to any disclaimer, the term of this patent is extended or adjusted under 35 U.S.C. 154(b) by 940 days.

(21) Appl. No.: 11/890,864

(22) Filed: Aug. 7, 2007

(65) Prior Publication Data

US 2009/0043512 A1 Feb. 12, 2009

(51) Int. Cl.
*G01N 33/48* (2006.01)
(52) U.S. Cl.
USPC .............................................. 702/19; 703/11
(58) Field of Classification Search
None
See application file for complete search history.

(56) References Cited

U.S. PATENT DOCUMENTS

| | | | |
|---|---|---|---|
| 7,231,301 B2 | 6/2007 | Doi et al. | |
| 2002/0150906 A1 | 10/2002 | Debe | |
| 2003/0130797 A1 | 7/2003 | Skolnick et al. | |
| 2004/0185486 A1 | 9/2004 | Zemla | |
| 2005/0089878 A1 | 4/2005 | Debe et al. | |

FOREIGN PATENT DOCUMENTS

| | | |
|---|---|---|
| WO | WO 93/01484 | 1/1993 |
| WO | WO 98/48270 | 10/1998 |
| WO | WO 00/11206 | 3/2000 |
| WO | WO 03/048724 | 6/2003 |

OTHER PUBLICATIONS

Zemla et al. Nucleic Acids Research, 2003, vol. 31, No. 13, p. 3370-3374.*
Cristobal et al. BMC Bioinformatics 2001, 2:5. Published Aug. 1, 2001.*
Zemla et al. Proteins: Structure, Function, and Genetics vol. 45, Issue S5, pp. 13-21, 2001.*
Al-Lazikani, B. et al., "Combining Multiple Structure and Sequence Alignments to Improve Sequence Detection and Alignment: Application to the SH2 Domains of Janus Kinases," *PNAS*, Dec. 18, 2001, pp. 14796-14801, vol. 98, No. 26.
Altschul, S.F. et al., "Gapped BLAST and PSI-BLAST: A New Generation of Protein Database Search Programs," *Nucleic Acids Research*, 1997, pp. 3389-3402, vol. 25.
Brady, G.P. et al., "Fast Prediction and Visualization of Protein Binding Pockets with PASS," *Journal of Computer-Aided Molecular Design*, 2000, pp. 383-401, vol. 14.
Bonneau, R. et al., "Functional Inferences from Blind ab Initio Protein Structure Predictions," *Journal of Structural Biology*, 2001, pp. 186-190, vol. 134.
Campbell, S. et al., "Ligand Binding: Functional Site Location, Similarity and Docking," *Current Opinion in Structural Biology*, 2003, pp. 389-395, vol. 13.
Canutescu, A. et al., A Graph-theory Algorithm for Rapid Protein Side-chain Prediction, *Protein Science*, 2003, pp. 2001-2014, vol. 12.
Fofanov, C. et al., "Fast Algorithm for the Analysis of the Presence of Short Oligonucleotide Subsequences in Genomic Sequences," *Technical Report No. UH-CS-05-11*, May 3, 2005, Department of Computer Science, University of Houston, USA, eight pages.
Fukunishi, Y. et al., "Similarities among Receptor Pockets and among Compounds: Analysis and Application to in silico Ligand Screening," *Journal of Molecular Graphics and Modelling*, 2005, pp. 34-45, vol. 24.
Gront, D. et al., "HCPM—Program for Hierarchical Clustering of Protein Models," *Bioinformatics*. Jul. 15, 2005, pp. 3179-3180, vol. 21, No. 14. Epub Apr. 19, 2005.
Holm, L. et al., "Protein Structure Comparison by Alignment of Distance Matrices," *Journal of Molecular Biology*, 1993, pp. 123-138, vol. 233.
Huan, J. et al., "Accurate Classification of Protein Structural Families Using Coherent Subgraph Analysis," *Pac. Symp. Biocomput*, 2004, pp. 411-422.
Lackner, P. et al., "ProSup: A Refined Tool for Protein Structure Alignment," *Protein Engineering*, 2000, pp. 745-752, vol. 13, No. 11.
Moult, J. et al., "Critical Assessment of Methods of Protein Structure Prediction (CASP)-round V", Proteins: Structure, Function, and Genetics, 2003, pp. 334-339, vol. 53, Issue S6.
Orengo, C.A. et al., "CATH-A Hierarchic Classification of Protein Domain Structures," *Structure*, 1997, pp. 1093-1108, vol. 5, No. 8.
Ortiz, A.R., "MAMMOTH (Matching Molecular Models Obtained from Theory): An Automated Method for Model Comparison," *Protein Science*, 2002, pp. 2606-2621, vol. 11.
Shindyalov, I. et al., "Protein Structure Alignment by Incremental Combinatorial Extension (CE) of the Optimal Path," *Protein Engineering*, 1998, pp. 739-747, vol. 11, No. 9.
Thompson, J. et al., "CLUSTAL W: improving the sensitivity of progressive multiple sequence alignment through sequence weighting, position-specific gap penalties and weight matrix choice," *Nucleic Acids Res.*, 1994, pp. 4673-4680, vol. 22.
Tramontano, A., et al. "Analysis and assessment of comparative modeling predictions in CASP4," *PROTEINS: Structure, Function, and Genetics*, 2001, pp. 22-38, vol. 45, Supp. 5.
United States Office Action, U.S. Appl. No. 10/782,061, Jan. 4, 2007, thirteen pages.
United States Office Action, U.S. Appl. No. 10/782,061, Sep. 24, 2007, fourteen pages.
United States Office Action, U.S. Appl. No. 10/782,061, Jun. 11, 2008, fifteen pages.
United States Office Action, U.S. Appl. No. 10/782,061, Jun. 23, 2009, fifteen pages.

(Continued)

*Primary Examiner* — Michael Borin
(74) *Attorney, Agent, or Firm* — Fenwick & West, LLP

(57) ABSTRACT

Disclosed are computational methods, and associated hardware and software products for scoring conservation in a protein structure based on a computationally identified family or cluster of protein structures. A method of computationally identifying a family or cluster of protein structures in also disclosed herein.

15 Claims, 12 Drawing Sheets

OTHER PUBLICATIONS

United States Office Action, U.S. Appl. No. 11/735,972, Dec. 23, 2010, eight pages.
United States Office Action, U.S. Appl. No. 11/735,981, Apr. 28, 2010, thirteen pages.
United States Office Action, U.S. Appl. No. 11/735,981, Jan. 6, 2011, twelve pages.
United States Office Action, U.S. Appl. No. 11/818,075, May 11, 2009, sixteen pages.
United States Office Action, U.S. Appl. No. 11/818,075, May 26, 2010, twenty pages.
United States Office Action, U.S. Appl. No. 11/818,075, Jan. 3, 2011.
United States Office Action, U.S. Appl. No. 11/890,863, Apr. 1, 2010, fourteen pages.
United States Office Action, U.S. Appl. No. 11/890,863, Dec. 20, 2010, twelve pages.
Zemla, A. et al., "AS2TS System for Protein Structure Modeling and Analysis," *Nucleic Acids Research*, 2005, pp. W111-W115, vol. 33, Web Server Issue.
Zemla, A. et al., LGA—A Method for Finding 3D Similarities in Protein Structures. *Nucleic Acids Research*, 2003, pp. 3370-3374, vol. 31.
Zemla, A. et al., "Processing and Analysis of CASP3 Protein Structure Predictions," *PROTEINS: Structure, Function, and Genetics*, 1999, pp. 22-29, vol. 27, Issue Suppl. 3.
Zemla, A. et al., "Processing and Evaluation of Predictions in CASP4," *PROTEINS: Structure, Function, and Genetics*, 2001, pp. 13-21, Supp. 5.
Zhang, C. et al., "Overview of Structural Genomics: From Structure to Function," *Current Opinion in Chemical Biology*, 2003, pp. 28-32, vol. 7.
Zhou, C. et al., "Computational Approaches for Identification of Conserved/Unique Binding Pockets in the A Chain of Ricin," *Bioinformatics*, May 19, 2005, pp. 3089-3096, vol. 21, No. 14.
Zhou, C. et al., "MannDB-A Microbial Database of Automated Protein Sequence Analyses and Evidence Integration for Protein Characterization," *BMC Bioinformatics*, Oct. 17, 2006, six pages.
Zhou, C. et al., "MvirDB-A Microbial Database of Protein Toxins, Virulence Factors and Antibiotic Resistance Genes for Bio-defence Applications," *Nucleic Acids Research*, 2006, pp. D1-D4, vol. 00, Database Issue.
Zu-Kang, F. et al., "Optimum Superimposition of Protein Structures: Ambiguities and Implications," Research Paper, *Folding & Design*, Feb. 26, 1996, pp. 123-132, vol. 1, No. 2, Salzburg, Austria.

\* cited by examiner

SEQUENCE LISTING

```
<160> NUMBER OF SEQ ID NOS: 171

<210> SEQ ID NO 1
<211> LENGTH: 23
<212> TYPE: PRT
<213> ORGANISM: Equine infectious anemia virus

<400> SEQUENCE: 1

Ile Val Leu Ile Asn Asp Thr Pro Leu Asn Val Leu Leu Asp Thr Gly
1               5                   10                  15

Ala Asp Thr Ser Val Leu Thr
            20

<210> SEQ ID NO 2
<211> LENGTH: 6
<212> TYPE: PRT
<213> ORGANISM: Equine infectious anemia virus

<400> SEQUENCE: 2

Lys Thr Arg Met Leu Val
1               5

<210> SEQ ID NO 3
<211> LENGTH: 14
<212> TYPE: PRT
<213> ORGANISM: Equine infectious anemia virus

<400> SEQUENCE: 3

Ile Pro Val Thr Ile Leu Gly Arg Asp Ile Leu Gln Asp Leu
1               5                   10

<210> SEQ ID NO 4
<211> LENGTH: 23
<212> TYPE: PRT
<213> ORGANISM: Human immunodeficiency virus

<400> SEQUENCE: 4

Thr Ile Lys Ile Gly Gly Gln Leu Lys Glu Ala Leu Leu Asp Thr Gly
1               5                   10                  15

Ala Asp Asp Thr Val Leu Glu
            20

<210> SEQ ID NO 5
<211> LENGTH: 6
<212> TYPE: PRT
<213> ORGANISM: Human immunodeficiency virus

<400> SEQUENCE: 5

Ile Gly Thr Val Leu Val
1               5

<210> SEQ ID NO 6
<211> LENGTH: 14
<212> TYPE: PRT
<213> ORGANISM: Human immunodeficiency virus

<400> SEQUENCE: 6

Thr Pro Val Asn Ile Ile Gly Arg Asn Leu Leu Thr Gln Ile
1               5                   10

<210> SEQ ID NO 7
<211> LENGTH: 23
<212> TYPE: PRT
```

<213> ORGANISM: Feline immunodeficiency virus

<400> SEQUENCE: 7

```
Leu Ile Phe Val Asn Gly Tyr Pro Ile Lys Phe Leu Asn Thr Gly
1               5                   10                  15

Ala Asp Ile Thr Ile Leu Asn
            20
```

<210> SEQ ID NO 8
<211> LENGTH: 6
<212> TYPE: PRT
<213> ORGANISM: Feline immunodeficiency virus

<400> SEQUENCE: 8

```
Phe Gly Asn Val Cys Val
1               5
```

<210> SEQ ID NO 9
<211> LENGTH: 14
<212> TYPE: PRT
<213> ORGANISM: Feline immunodeficiency virus

<400> SEQUENCE: 9

```
Leu Ile Gln Pro Leu Leu Gly Arg Asp Asn Met Ile Lys Phe
1               5                   10
```

<210> SEQ ID NO 10
<211> LENGTH: 23
<212> TYPE: PRT
<213> ORGANISM: Rous sarcoma virus

<400> SEQUENCE: 10

```
Arg Val Ile Leu Thr Ser Val Tyr Ile Thr Ala Leu Leu Asp Ser Gly
1               5                   10                  15

Ala Asp Ile Thr Ile Ile Ser
            20
```

<210> SEQ ID NO 11
<211> LENGTH: 6
<212> TYPE: PRT
<213> ORGANISM: Rous sarcoma virus

<400> SEQUENCE: 11

```
Leu Leu Phe Pro Ala Val
1               5
```

<210> SEQ ID NO 12
<211> LENGTH: 14
<212> TYPE: PRT
<213> ORGANISM: Rous sarcoma virus

<400> SEQUENCE: 12

```
Val Arg Gly Ser Ile Leu Gly Arg Asp Cys Leu Gln Gly Leu
1               5                   10
```

<210> SEQ ID NO 13
<211> LENGTH: 23
<212> TYPE: PRT
<213> ORGANISM: Avian myeloblastosis associated virus

<400> SEQUENCE: 13

```
Arg Val Ile Leu Thr Ser Val Tyr Ile Thr Ala Leu Leu Asp Ser Gly
1               5                   10                  15

Ala Asp Ile Thr Ile Ile Ser
            20
```

```
<210> SEQ ID NO 14
<211> LENGTH: 6
<212> TYPE: PRT
<213> ORGANISM: Avian myeloblastosis associated virus

<400> SEQUENCE: 14

Leu Leu Phe Pro Ala Val
1               5

<210> SEQ ID NO 15
<211> LENGTH: 14
<212> TYPE: PRT
<213> ORGANISM: Avian myeloblastosis associated virus

<400> SEQUENCE: 15

Val Arg Gly Ser Ile Leu Gly Arg Asp Cys Leu Gln Gly Leu
1               5                   10

<210> SEQ ID NO 16
<211> LENGTH: 23
<212> TYPE: PRT
<213> ORGANISM: Rous sarcoma virus

<400> SEQUENCE: 16

Arg Val Ile Leu Thr Ser Val Tyr Ile Thr Ala Leu Leu Asp Thr Gly
1               5                   10                  15

Ala Asp Asp Thr Val Ile Ser
            20

<210> SEQ ID NO 17
<211> LENGTH: 6
<212> TYPE: PRT
<213> ORGANISM: Rous sarcoma virus

<400> SEQUENCE: 17

Leu Leu Phe Pro Leu Val
1               5

<210> SEQ ID NO 18
<211> LENGTH: 14
<212> TYPE: PRT
<213> ORGANISM: Rous sarcoma virus

<400> SEQUENCE: 18

Thr Pro Val Asn Ile Leu Gly Arg Asp Cys Leu Gln Gly Leu
1               5                   10

<210> SEQ ID NO 19
<211> LENGTH: 23
<212> TYPE: PRT
<213> ORGANISM: Chimpanzee immunodeficiency virus

<400> SEQUENCE: 19

Thr Ala His Ile Glu Gly Gln Pro Val Glu Val Leu Leu Asp Thr Gly
1               5                   10                  15

Ala Asp Asp Ser Ile Val Thr
            20

<210> SEQ ID NO 20
<211> LENGTH: 6
<212> TYPE: PRT
<213> ORGANISM: Chimpanzee immunodeficiency virus
```

```
<400> SEQUENCE: 20

Lys Gly Thr Ile Met Thr
1               5

<210> SEQ ID NO 21
<211> LENGTH: 14
<212> TYPE: PRT
<213> ORGANISM: Chimpanzee immunodeficiency virus

<400> SEQUENCE: 21

Thr Pro Ile Asn Ile Phe Gly Arg Asn Leu Leu Thr Ala Leu
1               5                   10

<210> SEQ ID NO 22
<211> LENGTH: 23
<212> TYPE: PRT
<213> ORGANISM: Chimpanzee immunodeficiency virus

<400> SEQUENCE: 22

Thr Ala His Ile Glu Gly Gln Pro Val Glu Val Leu Leu Asp Thr Gly
1               5                   10                  15

Ala Asp Asp Ser Ile Val Thr
            20

<210> SEQ ID NO 23
<211> LENGTH: 6
<212> TYPE: PRT
<213> ORGANISM: Chimpanzee immunodeficiency virus

<400> SEQUENCE: 23

Arg Gly Thr Ile Met Thr
1               5

<210> SEQ ID NO 24
<211> LENGTH: 14
<212> TYPE: PRT
<213> ORGANISM: Chimpanzee immunodeficiency virus

<400> SEQUENCE: 24

Thr Pro Ile Asn Ile Phe Gly Arg Asn Leu Leu Thr Ala Leu
1               5                   10

<210> SEQ ID NO 25
<211> LENGTH: 23
<212> TYPE: PRT
<213> ORGANISM: Chimpanzee immunodeficiency virus

<400> SEQUENCE: 25

Thr Ala His Ile Glu Gly Gln Pro Val Glu Val Leu Leu Asp Thr Gly
1               5                   10                  15

Ala Asp Asp Ser Ile Val Thr
            20

<210> SEQ ID NO 26
<211> LENGTH: 6
<212> TYPE: PRT
<213> ORGANISM: Chimpanzee immunodeficiency virus

<400> SEQUENCE: 26

Lys Gly Thr Ile Met Thr
1               5

<210> SEQ ID NO 27
<211> LENGTH: 14
```

```
<212> TYPE: PRT
<213> ORGANISM: Chimpanzee immunodeficiency virus

<400> SEQUENCE: 27

Thr Pro Ile Asn Ile Phe Gly Arg Asn Leu Leu Thr Ala Leu
1               5                   10

<210> SEQ ID NO 28
<211> LENGTH: 23
<212> TYPE: PRT
<213> ORGANISM: Chimpanzee immunodeficiency virus

<400> SEQUENCE: 28

Thr Ala His Ile Glu Gly Gln Pro Val Glu Val Leu Leu Asp Thr Gly
1               5                   10                  15

Ala Asp Asp Ser Ile Val Thr
            20

<210> SEQ ID NO 29
<211> LENGTH: 6
<212> TYPE: PRT
<213> ORGANISM: Chimpanzee immunodeficiency virus

<400> SEQUENCE: 29

Lys Gly Thr Ile Met Thr
1               5

<210> SEQ ID NO 30
<211> LENGTH: 14
<212> TYPE: PRT
<213> ORGANISM: Chimpanzee immunodeficiency virus

<400> SEQUENCE: 30

Thr Pro Ile Asn Ile Phe Gly Arg Asn Leu Leu Thr Ala Leu
1               5                   10

<210> SEQ ID NO 31
<211> LENGTH: 23
<212> TYPE: PRT
<213> ORGANISM: Human immunodeficiency virus

<400> SEQUENCE: 31

Thr Ala Tyr Ile Glu Gly Gln Pro Val Glu Val Leu Leu Asp Thr Gly
1               5                   10                  15

Ala Asp Asp Ser Ile Val Ala
            20

<210> SEQ ID NO 32
<211> LENGTH: 6
<212> TYPE: PRT
<213> ORGANISM: Human immunodeficiency virus

<400> SEQUENCE: 32

Arg Ala Thr Ile Met Thr
1               5

<210> SEQ ID NO 33
<211> LENGTH: 14
<212> TYPE: PRT
<213> ORGANISM: Human immunodeficiency virus

<400> SEQUENCE: 33

Thr Pro Ile Asn Ile Phe Gly Arg Asn Ile Leu Thr Ala Leu
1               5                   10
```

```
<210> SEQ ID NO 34
<211> LENGTH: 23
<212> TYPE: PRT
<213> ORGANISM: Human immunodeficiency virus

<400> SEQUENCE: 34

Thr Ala Tyr Ile Glu Gly Gln Pro Val Glu Val Leu Leu Asp Thr Gly
1               5                   10                  15

Ala Asp Asp Ser Ile Val Ala
            20

<210> SEQ ID NO 35
<211> LENGTH: 6
<212> TYPE: PRT
<213> ORGANISM: Human immunodeficiency virus

<400> SEQUENCE: 35

Arg Ala Thr Ile Met Thr
1               5

<210> SEQ ID NO 36
<211> LENGTH: 14
<212> TYPE: PRT
<213> ORGANISM: Human immunodeficiency virus

<400> SEQUENCE: 36

Thr Pro Ile Asn Ile Phe Gly Arg Asn Ile Leu Thr Ala Leu
1               5                   10

<210> SEQ ID NO 37
<211> LENGTH: 23
<212> TYPE: PRT
<213> ORGANISM: Human immunodeficiency virus

<400> SEQUENCE: 37

Thr Ile Lys Ile Gly Gly Gln Leu Lys Glu Ala Leu Leu Asp Thr Gly
1               5                   10                  15

Ala Asp Asp Ser Ile Val Ala
            20

<210> SEQ ID NO 38
<211> LENGTH: 6
<212> TYPE: PRT
<213> ORGANISM: Human immunodeficiency virus

<400> SEQUENCE: 38

Ile Gly Thr Val Leu Val
1               5

<210> SEQ ID NO 39
<211> LENGTH: 14
<212> TYPE: PRT
<213> ORGANISM: Human immunodeficiency virus

<400> SEQUENCE: 39

Thr Pro Ile Asn Ile Ile Gly Arg Asn Leu Leu Thr Gln Ile
1               5                   10

<210> SEQ ID NO 40
<211> LENGTH: 23
<212> TYPE: PRT
<213> ORGANISM: Human immunodeficiency virus

<400> SEQUENCE: 40
```

```
Thr Ile Lys Ile Gly Gly Gln Leu Lys Glu Ala Leu Leu Asp Thr Gly
1               5                   10                  15

Ala Asp Asp Ser Ile Val Ala
            20

<210> SEQ ID NO 41
<211> LENGTH: 6
<212> TYPE: PRT
<213> ORGANISM: Human immunodeficiency virus

<400> SEQUENCE: 41

Ile Gly Thr Val Leu Val
1               5

<210> SEQ ID NO 42
<211> LENGTH: 14
<212> TYPE: PRT
<213> ORGANISM: Human immunodeficiency virus

<400> SEQUENCE: 42

Thr Pro Val Asn Ile Ile Gly Arg Asn Leu Leu Thr Gln Ile
1               5                   10

<210> SEQ ID NO 43
<211> LENGTH: 23
<212> TYPE: PRT
<213> ORGANISM: Human immunodeficiency virus

<400> SEQUENCE: 43

Thr Ile Lys Ile Gly Gly Gln Leu Lys Glu Ala Leu Leu Asp Thr Gly
1               5                   10                  15

Ala Asp Asp Thr Val Ile Glu
            20

<210> SEQ ID NO 44
<211> LENGTH: 6
<212> TYPE: PRT
<213> ORGANISM: Human immunodeficiency virus

<400> SEQUENCE: 44

Ile Gly Thr Val Leu Val
1               5

<210> SEQ ID NO 45
<211> LENGTH: 14
<212> TYPE: PRT
<213> ORGANISM: Human immunodeficiency virus

<400> SEQUENCE: 45

Thr Pro Ser Asn Ile Ile Gly Arg Asn Leu Leu Thr Gln Ile
1               5                   10

<210> SEQ ID NO 46
<211> LENGTH: 23
<212> TYPE: PRT
<213> ORGANISM: Human immunodeficiency virus

<400> SEQUENCE: 46

Thr Ile Lys Ile Gly Gly Gln Leu Lys Glu Ala Leu Leu Asp Thr Gly
1               5                   10                  15

Ala Asp Asp Thr Val Leu Glu
            20

<210> SEQ ID NO 47
```

```
<211> LENGTH: 6
<212> TYPE: PRT
<213> ORGANISM: Human immunodeficiency virus

<400> SEQUENCE: 47

Ile Gly Thr Val Leu Val
1               5

<210> SEQ ID NO 48
<211> LENGTH: 14
<212> TYPE: PRT
<213> ORGANISM: Human immunodeficiency virus

<400> SEQUENCE: 48

Thr Pro Val Asn Ile Ile Gly Arg Asn Leu Leu Thr Gln Ile
1               5                   10

<210> SEQ ID NO 49
<211> LENGTH: 23
<212> TYPE: PRT
<213> ORGANISM: Homo sapiens

<400> SEQUENCE: 49

Thr Ile Lys Ile Gly Gly Gln Leu Lys Glu Ala Leu Leu Asp Thr Gly
1               5                   10                  15

Ala Asp Asp Thr Val Ile Glu
            20

<210> SEQ ID NO 50
<211> LENGTH: 6
<212> TYPE: PRT
<213> ORGANISM: Homo sapiens

<400> SEQUENCE: 50

Ile Gly Thr Val Leu Val
1               5

<210> SEQ ID NO 51
<211> LENGTH: 14
<212> TYPE: PRT
<213> ORGANISM: Homo sapiens

<400> SEQUENCE: 51

Thr Pro Val Asn Ile Ile Gly Arg Asn Leu Leu Thr Gln Ile
1               5                   10

<210> SEQ ID NO 52
<211> LENGTH: 23
<212> TYPE: PRT
<213> ORGANISM: Feline immunodeficiency virus

<400> SEQUENCE: 52

Leu Ile Phe Val Asn Gly Tyr Pro Ile Lys Phe Leu Leu Asp Thr Gly
1               5                   10                  15

Ala Asp Ile Thr Ile Leu Asn
            20

<210> SEQ ID NO 53
<211> LENGTH: 6
<212> TYPE: PRT
<213> ORGANISM: Feline immunodeficiency virus

<400> SEQUENCE: 53

Phe Gly Asn Val Cys Val
1               5
```

```
<210> SEQ ID NO 54
<211> LENGTH: 14
<212> TYPE: PRT
<213> ORGANISM: Feline immunodeficiency virus

<400> SEQUENCE: 54

Leu Ile Gln Pro Leu Leu Gly Arg Asp Asn Met Ile Lys Phe
1               5                   10

<210> SEQ ID NO 55
<211> LENGTH: 23
<212> TYPE: PRT
<213> ORGANISM: Feline immunodeficiency virus

<400> SEQUENCE: 55

Leu Ile Phe Val Asn Gly Tyr Pro Ile Lys Phe Leu Leu Asp Thr Gly
1               5                   10                  15

Ala Asp Ile Thr Ile Leu Asn
            20

<210> SEQ ID NO 56
<211> LENGTH: 6
<212> TYPE: PRT
<213> ORGANISM: Feline immunodeficiency virus

<400> SEQUENCE: 56

Phe Gly Asn Val Cys Val
1               5

<210> SEQ ID NO 57
<211> LENGTH: 14
<212> TYPE: PRT
<213> ORGANISM: Feline immunodeficiency virus

<400> SEQUENCE: 57

Leu Ile Val Pro Leu Leu Gly Arg Asp Asn Met Ile Lys Phe
1               5                   10

<210> SEQ ID NO 58
<211> LENGTH: 5
<212> TYPE: PRT
<213> ORGANISM: Homo sapiens

<400> SEQUENCE: 58

Gly Ala Ser Leu Ile
1               5

<210> SEQ ID NO 59
<211> LENGTH: 4
<212> TYPE: PRT
<213> ORGANISM: Homo sapiens

<400> SEQUENCE: 59

Asp Arg Trp Val
1

<210> SEQ ID NO 60
<211> LENGTH: 5
<212> TYPE: PRT
<213> ORGANISM: Homo sapiens

<400> SEQUENCE: 60

Thr Ala Ala His Cys
1               5
```

```
<210> SEQ ID NO 61
<211> LENGTH: 4
<212> TYPE: PRT
<213> ORGANISM: Homo sapiens

<400> SEQUENCE: 61

Leu Val Arg Ile
1

<210> SEQ ID NO 62
<211> LENGTH: 4
<212> TYPE: PRT
<213> ORGANISM: Homo sapiens

<400> SEQUENCE: 62

Ile Ser Met Leu
1

<210> SEQ ID NO 63
<211> LENGTH: 6
<212> TYPE: PRT
<213> ORGANISM: Homo sapiens

<400> SEQUENCE: 63

Ile Ala Leu Met Lys Leu
1               5

<210> SEQ ID NO 64
<211> LENGTH: 5
<212> TYPE: PRT
<213> ORGANISM: Homo sapiens

<400> SEQUENCE: 64

Gly Gly Ser Leu Ile
1               5

<210> SEQ ID NO 65
<211> LENGTH: 4
<212> TYPE: PRT
<213> ORGANISM: Homo sapiens

<400> SEQUENCE: 65

Glu Gln Trp Val
1

<210> SEQ ID NO 66
<211> LENGTH: 5
<212> TYPE: PRT
<213> ORGANISM: Homo sapiens

<400> SEQUENCE: 66

Ser Ala Ala His Cys
1               5

<210> SEQ ID NO 67
<211> LENGTH: 4
<212> TYPE: PRT
<213> ORGANISM: Homo sapiens

<400> SEQUENCE: 67

Gln Val Arg Leu
1

<210> SEQ ID NO 68
```

<211> LENGTH: 4
<212> TYPE: PRT
<213> ORGANISM: Homo sapiens

<400> SEQUENCE: 68

Phe Ile Asn Ala
1

<210> SEQ ID NO 69
<211> LENGTH: 6
<212> TYPE: PRT
<213> ORGANISM: Homo sapiens

<400> SEQUENCE: 69

Ile Met Leu Ile Lys Leu
1               5

<210> SEQ ID NO 70
<211> LENGTH: 5
<212> TYPE: PRT
<213> ORGANISM: Homo sapiens

<400> SEQUENCE: 70

Gly Gly Ile Leu Ile
1               5

<210> SEQ ID NO 71
<211> LENGTH: 4
<212> TYPE: PRT
<213> ORGANISM: Homo sapiens

<400> SEQUENCE: 71

Ser Cys Trp Ile
1

<210> SEQ ID NO 72
<211> LENGTH: 5
<212> TYPE: PRT
<213> ORGANISM: Homo sapiens

<400> SEQUENCE: 72

Ser Ala Ala His Cys
1               5

<210> SEQ ID NO 73
<211> LENGTH: 4
<212> TYPE: PRT
<213> ORGANISM: Homo sapiens

<400> SEQUENCE: 73

Thr Val Ile Leu
1

<210> SEQ ID NO 74
<211> LENGTH: 4
<212> TYPE: PRT
<213> ORGANISM: Homo sapiens

<400> SEQUENCE: 74

Lys Phe Glu Val
1

<210> SEQ ID NO 75
<211> LENGTH: 6
<212> TYPE: PRT
<213> ORGANISM: Homo sapiens

<400> SEQUENCE: 75

Ile Ala Leu Leu Gln Leu
1               5

<210> SEQ ID NO 76
<211> LENGTH: 5
<212> TYPE: PRT
<213> ORGANISM: Bos taurus

<400> SEQUENCE: 76

Gly Gly Ser Leu Ile
1               5

<210> SEQ ID NO 77
<211> LENGTH: 4
<212> TYPE: PRT
<213> ORGANISM: Bos taurus

<400> SEQUENCE: 77

Ser Gln Trp Val
1

<210> SEQ ID NO 78
<211> LENGTH: 5
<212> TYPE: PRT
<213> ORGANISM: Bos taurus

<400> SEQUENCE: 78

Ser Ala Ala His Cys
1               5

<210> SEQ ID NO 79
<211> LENGTH: 4
<212> TYPE: PRT
<213> ORGANISM: Bos taurus

<400> SEQUENCE: 79

Gln Val Arg Leu
1

<210> SEQ ID NO 80
<211> LENGTH: 4
<212> TYPE: PRT
<213> ORGANISM: Bos taurus

<400> SEQUENCE: 80

Phe Ile Ser Ala
1

<210> SEQ ID NO 81
<211> LENGTH: 6
<212> TYPE: PRT
<213> ORGANISM: Bos taurus

<400> SEQUENCE: 81

Ile Met Leu Ile Lys Leu
1               5

<210> SEQ ID NO 82
<211> LENGTH: 5
<212> TYPE: PRT
<213> ORGANISM: Sus scrofa

<400> SEQUENCE: 82

Gly Gly Ser Leu Ile
1               5

<210> SEQ ID NO 83
<211> LENGTH: 4
<212> TYPE: PRT
<213> ORGANISM: Sus scrofa

<400> SEQUENCE: 83

Ser Gln Trp Val
1

<210> SEQ ID NO 84
<211> LENGTH: 5
<212> TYPE: PRT
<213> ORGANISM: Sus scrofa

<400> SEQUENCE: 84

Ser Ala Ala His Cys
1               5

<210> SEQ ID NO 85
<211> LENGTH: 4
<212> TYPE: PRT
<213> ORGANISM: Sus scrofa

<400> SEQUENCE: 85

Gln Val Arg Leu
1

<210> SEQ ID NO 86
<211> LENGTH: 4
<212> TYPE: PRT
<213> ORGANISM: Sus scrofa

<400> SEQUENCE: 86

Phe Ile Asn Ala
1

<210> SEQ ID NO 87
<211> LENGTH: 6
<212> TYPE: PRT
<213> ORGANISM: Sus scrofa

<400> SEQUENCE: 87

Ile Met Leu Ile Lys Leu
1               5

<210> SEQ ID NO 88
<211> LENGTH: 5
<212> TYPE: PRT
<213> ORGANISM: Bos taurus

<400> SEQUENCE: 88

Gly Gly Ser Leu Ile
1               5

<210> SEQ ID NO 89
<211> LENGTH: 4
<212> TYPE: PRT
<213> ORGANISM: Bos taurus

<400> SEQUENCE: 89

Ser Gln Trp Val
1

```
<210> SEQ ID NO 90
<211> LENGTH: 5
<212> TYPE: PRT
<213> ORGANISM: Bos taurus

<400> SEQUENCE: 90

Ser Ala Ala His Cys
1               5

<210> SEQ ID NO 91
<211> LENGTH: 4
<212> TYPE: PRT
<213> ORGANISM: Bos taurus

<400> SEQUENCE: 91

Gln Val Arg Leu
1

<210> SEQ ID NO 92
<211> LENGTH: 4
<212> TYPE: PRT
<213> ORGANISM: Bos taurus

<400> SEQUENCE: 92

Phe Ile Ser Ala
1

<210> SEQ ID NO 93
<211> LENGTH: 6
<212> TYPE: PRT
<213> ORGANISM: Bos taurus

<400> SEQUENCE: 93

Ile Met Leu Ile Lys Leu
1               5

<210> SEQ ID NO 94
<211> LENGTH: 5
<212> TYPE: PRT
<213> ORGANISM: Rattus rattus

<400> SEQUENCE: 94

Gly Gly Ser Leu Ile
1               5

<210> SEQ ID NO 95
<211> LENGTH: 4
<212> TYPE: PRT
<213> ORGANISM: Rattus rattus

<400> SEQUENCE: 95

Asp Gln Trp Val
1

<210> SEQ ID NO 96
<211> LENGTH: 5
<212> TYPE: PRT
<213> ORGANISM: Rattus rattus

<400> SEQUENCE: 96

Ser Ala Ala His Cys
1               5

<210> SEQ ID NO 97
<211> LENGTH: 4
```

```
<212> TYPE: PRT
<213> ORGANISM: Rattus rattus

<400> SEQUENCE: 97

Gln Val Arg Leu
1

<210> SEQ ID NO 98
<211> LENGTH: 4
<212> TYPE: PRT
<213> ORGANISM: Rattus rattus

<400> SEQUENCE: 98

Phe Val Asn Ala
1

<210> SEQ ID NO 99
<211> LENGTH: 6
<212> TYPE: PRT
<213> ORGANISM: Rattus rattus

<400> SEQUENCE: 99

Ile Met Leu Ile Lys Leu
1               5

<210> SEQ ID NO 100
<211> LENGTH: 5
<212> TYPE: PRT
<213> ORGANISM: Salmo salar

<400> SEQUENCE: 100

Gly Gly Ser Leu Val
1               5

<210> SEQ ID NO 101
<211> LENGTH: 4
<212> TYPE: PRT
<213> ORGANISM: Salmo salar

<400> SEQUENCE: 101

Glu Asn Trp Val
1

<210> SEQ ID NO 102
<211> LENGTH: 5
<212> TYPE: PRT
<213> ORGANISM: Salmo salar

<400> SEQUENCE: 102

Ser Ala Ala His Cys
1               5

<210> SEQ ID NO 103
<211> LENGTH: 4
<212> TYPE: PRT
<213> ORGANISM: Salmo salar

<400> SEQUENCE: 103

Glu Val Arg Leu
1

<210> SEQ ID NO 104
<211> LENGTH: 4
<212> TYPE: PRT
<213> ORGANISM: Salmo salar
```

```
<400> SEQUENCE: 104

Phe Ile Ser Ser
1

<210> SEQ ID NO 105
<211> LENGTH: 6
<212> TYPE: PRT
<213> ORGANISM: Salmo salar

<400> SEQUENCE: 105

Ile Met Leu Ile Lys Leu
1               5

<210> SEQ ID NO 106
<211> LENGTH: 5
<212> TYPE: PRT
<213> ORGANISM: Mus musculus

<400> SEQUENCE: 106

Gly Gly Val Leu Leu
1               5

<210> SEQ ID NO 107
<211> LENGTH: 4
<212> TYPE: PRT
<213> ORGANISM: Mus musculus

<400> SEQUENCE: 107

Arg Asn Trp Val
1

<210> SEQ ID NO 108
<211> LENGTH: 5
<212> TYPE: PRT
<213> ORGANISM: Mus musculus

<400> SEQUENCE: 108

Thr Ala Ala His Cys
1               5

<210> SEQ ID NO 109
<211> LENGTH: 4
<212> TYPE: PRT
<213> ORGANISM: Mus musculus

<400> SEQUENCE: 109

Glu Val Trp Leu
1

<210> SEQ ID NO 110
<211> LENGTH: 4
<212> TYPE: PRT
<213> ORGANISM: Mus musculus

<400> SEQUENCE: 110

His Arg Leu Val
1

<210> SEQ ID NO 111
<211> LENGTH: 6
<212> TYPE: PRT
<213> ORGANISM: Mus musculus

<400> SEQUENCE: 111

Leu Met Leu Leu Arg Leu
```

```
<210> SEQ ID NO 112
<211> LENGTH: 5
<212> TYPE: PRT
<213> ORGANISM: Rattus norvegicus

<400> SEQUENCE: 112

Gly Gly Ser Leu Ile
1               5

<210> SEQ ID NO 113
<211> LENGTH: 4
<212> TYPE: PRT
<213> ORGANISM: Rattus norvegicus

<400> SEQUENCE: 113

Asp Gln Trp Val
1

<210> SEQ ID NO 114
<211> LENGTH: 5
<212> TYPE: PRT
<213> ORGANISM: Rattus norvegicus

<400> SEQUENCE: 114

Ser Ala Ala His Cys
1               5

<210> SEQ ID NO 115
<211> LENGTH: 4
<212> TYPE: PRT
<213> ORGANISM: Rattus norvegicus

<400> SEQUENCE: 115

Gln Val Arg Leu
1

<210> SEQ ID NO 116
<211> LENGTH: 4
<212> TYPE: PRT
<213> ORGANISM: Rattus norvegicus

<400> SEQUENCE: 116

Phe Val Asn Ala
1

<210> SEQ ID NO 117
<211> LENGTH: 6
<212> TYPE: PRT
<213> ORGANISM: Rattus norvegicus

<400> SEQUENCE: 117

Ile Met Leu Ile Lys Leu
1               5

<210> SEQ ID NO 118
<211> LENGTH: 5
<212> TYPE: PRT
<213> ORGANISM: Sus scrofa

<400> SEQUENCE: 118

Gly Gly Thr Leu Ile
1               5
```

```
<210> SEQ ID NO 119
<211> LENGTH: 4
<212> TYPE: PRT
<213> ORGANISM: Sus scrofa

<400> SEQUENCE: 119

Gln Asn Trp Val
1

<210> SEQ ID NO 120
<211> LENGTH: 5
<212> TYPE: PRT
<213> ORGANISM: Sus scrofa

<400> SEQUENCE: 120

Thr Ala Ala His Cys
1               5

<210> SEQ ID NO 121
<211> LENGTH: 4
<212> TYPE: PRT
<213> ORGANISM: Sus scrofa

<400> SEQUENCE: 121

Arg Val Val Val
1

<210> SEQ ID NO 122
<211> LENGTH: 4
<212> TYPE: PRT
<213> ORGANISM: Sus scrofa

<400> SEQUENCE: 122

Tyr Val Gly Val
1

<210> SEQ ID NO 123
<211> LENGTH: 6
<212> TYPE: PRT
<213> ORGANISM: Sus scrofa

<400> SEQUENCE: 123

Ile Ala Leu Leu Arg Leu
1               5

<210> SEQ ID NO 124
<211> LENGTH: 5
<212> TYPE: PRT
<213> ORGANISM: Homo sapiens

<400> SEQUENCE: 124

Gly Gly Ser Leu Ile
1               5

<210> SEQ ID NO 125
<211> LENGTH: 4
<212> TYPE: PRT
<213> ORGANISM: Homo sapiens

<400> SEQUENCE: 125

Pro Cys Trp Val
1

<210> SEQ ID NO 126
<211> LENGTH: 5
<212> TYPE: PRT
```

```
<213> ORGANISM: Homo sapiens

<400> SEQUENCE: 126

Ser Ala Thr His Cys
1               5

<210> SEQ ID NO 127
<211> LENGTH: 4
<212> TYPE: PRT
<213> ORGANISM: Homo sapiens

<400> SEQUENCE: 127

Ile Val Tyr Leu
1

<210> SEQ ID NO 128
<211> LENGTH: 4
<212> TYPE: PRT
<213> ORGANISM: Homo sapiens

<400> SEQUENCE: 128

Lys Phe Glu Val
1

<210> SEQ ID NO 129
<211> LENGTH: 6
<212> TYPE: PRT
<213> ORGANISM: Homo sapiens

<400> SEQUENCE: 129

Ile Ala Leu Leu Lys Ile
1               5

<210> SEQ ID NO 130
<211> LENGTH: 5
<212> TYPE: PRT
<213> ORGANISM: Agkistrodon acutus

<400> SEQUENCE: 130

Gly Gly Thr Leu Ile
1               5

<210> SEQ ID NO 131
<211> LENGTH: 4
<212> TYPE: PRT
<213> ORGANISM: Agkistrodon acutus

<400> SEQUENCE: 131

Pro Glu Trp Val
1

<210> SEQ ID NO 132
<211> LENGTH: 5
<212> TYPE: PRT
<213> ORGANISM: Agkistrodon acutus

<400> SEQUENCE: 132

Thr Ala Ala His Cys
1               5

<210> SEQ ID NO 133
<211> LENGTH: 4
<212> TYPE: PRT
<213> ORGANISM: Agkistrodon acutus

<400> SEQUENCE: 133
```

Gln Met Gln Leu
1

<210> SEQ ID NO 134
<211> LENGTH: 4
<212> TYPE: PRT
<213> ORGANISM: Agkistrodon acutus

<400> SEQUENCE: 134

Thr Arg Asn Pro
1

<210> SEQ ID NO 135
<211> LENGTH: 6
<212> TYPE: PRT
<213> ORGANISM: Agkistrodon acutus

<400> SEQUENCE: 135

Ile Met Leu Ile Lys Leu
1               5

<210> SEQ ID NO 136
<211> LENGTH: 5
<212> TYPE: PRT
<213> ORGANISM: Homo sapiens

<400> SEQUENCE: 136

Gly Gly Ser Leu Met
1               5

<210> SEQ ID NO 137
<211> LENGTH: 4
<212> TYPE: PRT
<213> ORGANISM: Homo sapiens

<400> SEQUENCE: 137

Pro Cys Trp Val
1

<210> SEQ ID NO 138
<211> LENGTH: 5
<212> TYPE: PRT
<213> ORGANISM: Homo sapiens

<400> SEQUENCE: 138

Ser Ala Thr His Cys
1               5

<210> SEQ ID NO 139
<211> LENGTH: 4
<212> TYPE: PRT
<213> ORGANISM: Homo sapiens

<400> SEQUENCE: 139

Ile Val Tyr Leu
1

<210> SEQ ID NO 140
<211> LENGTH: 4
<212> TYPE: PRT
<213> ORGANISM: Homo sapiens

<400> SEQUENCE: 140

Lys Phe Glu Val
1

<210> SEQ ID NO 141
<211> LENGTH: 6
<212> TYPE: PRT
<213> ORGANISM: Homo sapiens

<400> SEQUENCE: 141

Ile Ala Leu Leu Lys Ile
1               5

<210> SEQ ID NO 142
<211> LENGTH: 5
<212> TYPE: PRT
<213> ORGANISM: Homo sapiens

<400> SEQUENCE: 142

Gly Gly Ser Leu Met
1               5

<210> SEQ ID NO 143
<211> LENGTH: 4
<212> TYPE: PRT
<213> ORGANISM: Homo sapiens

<400> SEQUENCE: 143

Pro Cys Trp Val
1

<210> SEQ ID NO 144
<211> LENGTH: 5
<212> TYPE: PRT
<213> ORGANISM: Homo sapiens

<400> SEQUENCE: 144

Ser Ala Thr His Cys
1               5

<210> SEQ ID NO 145
<211> LENGTH: 4
<212> TYPE: PRT
<213> ORGANISM: Homo sapiens

<400> SEQUENCE: 145

Ile Val Tyr Leu
1

<210> SEQ ID NO 146
<211> LENGTH: 4
<212> TYPE: PRT
<213> ORGANISM: Homo sapiens

<400> SEQUENCE: 146

Lys Phe Glu Val
1

<210> SEQ ID NO 147
<211> LENGTH: 6
<212> TYPE: PRT
<213> ORGANISM: Homo sapiens

<400> SEQUENCE: 147

Ile Ala Leu Leu Lys Ile
1               5

<210> SEQ ID NO 148

```
<211> LENGTH: 5
<212> TYPE: PRT
<213> ORGANISM: Homo sapiens

<400> SEQUENCE: 148

Gly Gly Ile Leu Ile
1               5

<210> SEQ ID NO 149
<211> LENGTH: 4
<212> TYPE: PRT
<213> ORGANISM: Homo sapiens

<400> SEQUENCE: 149

Ser Cys Trp Ile
1

<210> SEQ ID NO 150
<211> LENGTH: 5
<212> TYPE: PRT
<213> ORGANISM: Homo sapiens

<400> SEQUENCE: 150

Ser Ala Ala His Cys
1               5

<210> SEQ ID NO 151
<211> LENGTH: 4
<212> TYPE: PRT
<213> ORGANISM: Homo sapiens

<400> SEQUENCE: 151

Thr Val Ile Leu
1

<210> SEQ ID NO 152
<211> LENGTH: 4
<212> TYPE: PRT
<213> ORGANISM: Homo sapiens

<400> SEQUENCE: 152

Lys Phe Glu Val
1

<210> SEQ ID NO 153
<211> LENGTH: 6
<212> TYPE: PRT
<213> ORGANISM: Homo sapiens

<400> SEQUENCE: 153

Ile Ala Leu Leu Gln Leu
1               5

<210> SEQ ID NO 154
<211> LENGTH: 5
<212> TYPE: PRT
<213> ORGANISM: Eisenia foetida

<400> SEQUENCE: 154

Gly Ala Ser Leu Leu
1               5

<210> SEQ ID NO 155
<211> LENGTH: 4
<212> TYPE: PRT
<213> ORGANISM: Eisenia foetida
```

```
<400> SEQUENCE: 155

Ser Thr Ser Ala
1

<210> SEQ ID NO 156
<211> LENGTH: 5
<212> TYPE: PRT
<213> ORGANISM: Eisenia foetida

<400> SEQUENCE: 156

Ser Ala Ser His Cys
1               5

<210> SEQ ID NO 157
<211> LENGTH: 4
<212> TYPE: PRT
<213> ORGANISM: Eisenia foetida

<400> SEQUENCE: 157

Arg Val Ile Ala
1

<210> SEQ ID NO 158
<211> LENGTH: 4
<212> TYPE: PRT
<213> ORGANISM: Eisenia foetida

<400> SEQUENCE: 158

Thr Ala Asn Val
1

<210> SEQ ID NO 159
<211> LENGTH: 6
<212> TYPE: PRT
<213> ORGANISM: Eisenia foetida

<400> SEQUENCE: 159

Ile Ala Ile Leu His Leu
1               5

<210> SEQ ID NO 160
<211> LENGTH: 5
<212> TYPE: PRT
<213> ORGANISM: Homo sapiens

<400> SEQUENCE: 160

Gly Gly Ser Leu Ile
1               5

<210> SEQ ID NO 161
<211> LENGTH: 4
<212> TYPE: PRT
<213> ORGANISM: Homo sapiens

<400> SEQUENCE: 161

Pro Gln Trp Val
1

<210> SEQ ID NO 162
<211> LENGTH: 5
<212> TYPE: PRT
<213> ORGANISM: Homo sapiens

<400> SEQUENCE: 162
```

Thr Ala Ala His Cys
1               5

<210> SEQ ID NO 163
<211> LENGTH: 4
<212> TYPE: PRT
<213> ORGANISM: Homo sapiens

<400> SEQUENCE: 163

Arg Val Gln Leu
1

<210> SEQ ID NO 164
<211> LENGTH: 4
<212> TYPE: PRT
<213> ORGANISM: Homo sapiens

<400> SEQUENCE: 164

Leu Leu Pro Val
1

<210> SEQ ID NO 165
<211> LENGTH: 6
<212> TYPE: PRT
<213> ORGANISM: Homo sapiens

<400> SEQUENCE: 165

Ile Ala Leu Leu Glu Leu
1               5

<210> SEQ ID NO 166
<211> LENGTH: 5
<212> TYPE: PRT
<213> ORGANISM: Homo sapiens

<400> SEQUENCE: 166

Gly Gly Ala Leu Ile
1               5

<210> SEQ ID NO 167
<211> LENGTH: 4
<212> TYPE: PRT
<213> ORGANISM: Homo sapiens

<400> SEQUENCE: 167

Ala Arg Phe Val
1

<210> SEQ ID NO 168
<211> LENGTH: 5
<212> TYPE: PRT
<213> ORGANISM: Homo sapiens

<400> SEQUENCE: 168

Thr Ala Ala Ser Cys
1               5

<210> SEQ ID NO 169
<211> LENGTH: 4
<212> TYPE: PRT
<213> ORGANISM: Homo sapiens

<400> SEQUENCE: 169

Thr Val Val Leu
1

```
<210> SEQ ID NO 170
<211> LENGTH: 4
<212> TYPE: PRT
<213> ORGANISM: Homo sapiens

<400> SEQUENCE: 170

Thr Phe Ser Ile
1

<210> SEQ ID NO 171
<211> LENGTH: 6
<212> TYPE: PRT
<213> ORGANISM: Homo sapiens

<400> SEQUENCE: 171

Leu Met Leu Leu Gln Leu
1               5
```

STRUCTURE-SEQUENCE BASED ANALYSIS FOR IDENTIFICATION OF CONSERVED REGIONS IN PROTEINS

STATEMENT REGARDING FEDERALLY FUNDED RESEARCH

The United States Government has rights in this invention pursuant to Contract No. W-7405-ENG-48 between the United States Department of Energy and the University of California, for the operation of Lawrence Livermore National Laboratory.

CROSS REFERENCE TO RELATED APPLICATION

Not applicable

TECHNICAL FIELD

The disclosed embodiments generally relate to structural bioinformatics. Specifically, the disclosed embodiments relate to methods for scoring residue conservation within a family of protein structures.

BACKGROUND

Bioinformatics is an area of research which employs applied computer science, mathematics and physics to solve biological problems. Structural bioinformatics refers to the use of bioinformatics to solve the unique set of biological problems which relate to the three dimensional structures of polypeptide or protein sequences, herein referred to as protein structures. Protein structures are sets of atomic coordinates representative of a three dimensional structure of a protein. Atom coordinates may be determined computationally or experimentally by using a variety of techniques such as x-ray crystallography, electron microscopy and nuclear magnetic resonance spectroscopy.

Conservation is the phenomenon by which residues or polypeptides in homologous protein structures are subject to lower rates of substitution than other parts of the protein structure. Conservation is thought to be representative of structural and functional importance of these residues and polypeptides. Obtaining an accurate characterization of conservation in a protein structure therefore is critical for addressing biological problems such as targeted drug design and pathogen detection.

Conservation is a relative value because substitution rates for residues are determined relative to a set of homologous protein structures. Consequently, identifying a proper set of homologous protein structures for a given protein structure is a prerequisite for obtaining a good characterization of conservation in the protein structure.

Identifying a set of homologous protein structures for a given protein structure is complicated by the fact that a single metric will not usually provide an optimal indication of protein homology. This is largely due to variability of conservation in different domains of protein structures. For instance, proteins with overall similarity in structure, herein referred to as global similarity, may not have good local correspondence between domains. Conversely, proteins that have a high degree of local similarity due to evolutionarily conserved domains may not always have good global similarity due to structurally variable or unstructured regions, such as loops.

Therefore, one of the best methods in characterizing the conservation in a protein structure is to determine a family or category of related protein structures to which the protein structure belongs. However, the identification of the family of protein structures is also complicated for the above reasons.

Thus, there is a need in the art for improved methods of characterizing conservation in protein structures. The present invention addresses these and other shortcomings of the prior art.

SUMMARY OF THE INVENTION

These needs are met by methods and computer program products for of scoring a set of residues within a cluster of proteins.

Embodiments of this method comprise generating a plurality of pair-wise protein structure alignments between a plurality of protein structures. The method comprises determining that a set of protein structures from the plurality of protein structures form a cluster of protein structures based on a plurality of pair-wise local homology values and a plurality of pair-wise global homology values, wherein the plurality of pair-wise local homology values and the plurality of pair-wise global homology values are based on the plurality of pair-wise structural alignments. The method further comprises identifying a span, wherein each span comprises a set of one-to-one correspondences of residues that are within a first pre-determined distance of each other based on the plurality of pair-wise structural alignments of the cluster of protein structures. The method further comprises generating a plurality of conservation scores, wherein the conservation scores are based on a similarity metric and are generated for the set of one-to-one correspondences of residues. The method further comprises storing the plurality of conservation scores.

In another aspect, the present invention may be embodied as a computer-readable storage medium on which is encoded computer program code for clustering a set of three dimensional protein structures according to the above described method.

The features and advantages described herein are not all-inclusive and, in particular, many additional features and advantages will be apparent to one of ordinary skill in the art in view of the figures and description. Moreover, it should be noted that the language used in the specification has been principally selected for readability and instructional purposes, and not to limit the scope of the inventive subject matter

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 6 illustrates a multiple sequence structure alignment (SEQ ID NOS 1-57, respectively, in order of appearance) of cluster #1 showing the "spans" or locally aligned regions in cluster #1.

FIG. 10 illustrates a multiple sequence structure alignment (SEQ ID NOS 58-171, respectively, in order of appearance) of cluster #1 showing the "spans" or locally aligned regions in cluster #1.

Figure 1:
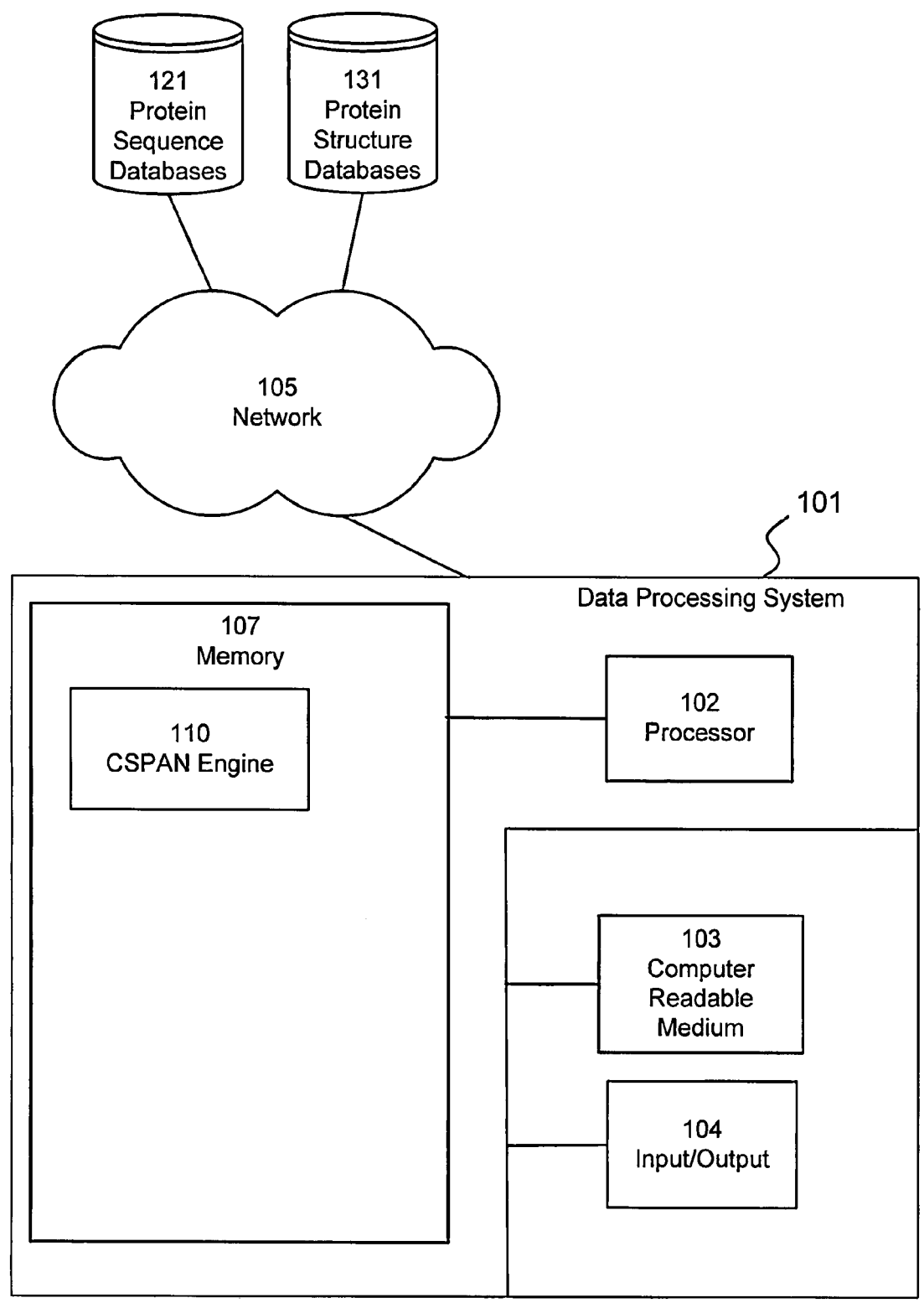
FIG. 1 illustrates a system architecture adapted to support one embodiment.

The figures depict various embodiments of the present invention for purposes of illustration only. One skilled in the art will readily recognize from the following discussion that alternative embodiments of the structures and methods illustrated herein may be employed without departing from the principles of the invention described herein.

DEFINITIONS

Residue: An amino acid residue is one amino acid that is joined to another by a peptide bond. Residue is referred to herein to describe both an amino acid and its position in a polypeptide sequence.

Surface residue: A surface residue is a residue located on a surface of a polypeptide. In contrast, a buried residue is a residue that is not located on the surface of a polypeptide. A surface residue usually includes a hydrophilic side chain. Operationally, a surface residue can be identified computationally from a structural model of a polypeptide as a residue that contacts a sphere of hydration rolled over the surface of the molecular structure. A surface residue also can be identified experimentally through the use of deuterium exchange studies, or accessibility to various labeling reagents such as, e.g., hydrophilic alkylating agents.

Polypeptide: A single linear chain of 2 or more amino acids. A protein is an example of a polypeptide.

Local Alignment: A local alignment is the identification of local similarities in an alignment or superposition of data. In reference to protein structure alignment, a local alignment refers to pairs of corresponding residues whose co-ordinate positions do not differ by more than a small number of Angstroms (e.g. 0.5 Angstroms) based on the superposition of their respective protein structures.

Global Alignment: A global alignment refers to the overall alignment or superposition of two sets of data. In protein structure alignment, metrics used to define global alignment include root mean square deviation (RMSD) or global distance test (GDT).

Contiguous residues: Contiguous residues are residues or pairs of residues which are sequentially contiguous in a polypeptide sequence, a sequence alignment or a structural correspondence.

Homolog: A gene related to a second gene by descent from a common ancestral DNA sequence. The term, homolog, may apply to the relationship between genes separated by a speciation event or to the relationship between genes separated by a genetic duplication event. Organisms that are un-related or distantly related though evolution may contain homologous sequences due to convergent evolution or targeted manipulated of their genetic material.

Conservation: Conservation refers to the degree of similarity in the primary or secondary structure of molecules between homologs. In reference to an individual residue or amino acid, conservation is used to refer to a computed likelihood of substitution or deletion based on comparison with homologous molecules. Residues that are strongly conserved are thought to be functionally or structurally important portions of the molecule.

GDT Matrix: Distance matrices are used to present the results of the calculation of an optimal pair-wise alignment score. A GDT matrix is a type of distance matrix. In GDT matrices, the matrix field (i,j) is the score (number of residues superimposed under a given distance cutoff) assigned to the optimal alignment between two residues (up to a total of i by j residues) from the input structures. Each entry is calculated from the top-left neighboring entries by way of a recursive equation.

Substitution Matrix: A matrix that defines scores for amino acid substitutions, reflecting the similarity of physicochemical properties, and observed substitution frequencies. These matrices are the foundation of statistical techniques for finding alignments.

DETAILED DESCRIPTION OF THE DRAWINGS

Embodiments are now described with reference to the figures where like reference numbers indicate identical or functionally similar elements.

FIG. 1 shows a system architecture adapted to support one embodiment of the CSPAN Engine. The system architecture includes a network 105, through which any number of Protein Structure Databases 131 and Protein Sequence Databases 121 are accessed by a data processing system 101.

FIG. 1 shows component engines used to generate and characterize protein motifs. The data processing system 101 includes the CSPAN Engine 110. Each of the foregoing is implemented, in one embodiment, as software modules (or programs) executed by processor 102.

The CSPAN Engine 110 operates to import and/or generate a set of protein structures by accessing the Protein Sequence Databases 121 and Protein Structure Databases 131 through the network 105 (as operationally and programmatically defined within the data processing system).

It should also be appreciated that in practice at least some of the components of the data processing system 101 will be distributed over multiple computers, communicating over a network. For example, the CSPAN Engine 110 may be deployed over multiple servers. As another example, the CSPAN Engine 110 may be located on any number of different computers. For convenience of explanation, however, the components of the data processing system 101 are discussed as though they were implemented on a single computer.

In another embodiment, some or all of the Protein Sequence Databases 121 and the Protein Structure Databases 131 are located on the data processing system 101 instead of being coupled to the data processing system 101 by a network 105. For example, the CSPAN Engine 110 may import protein sequence from Protein Structure Databases 131 that are a part of or associated with the data processing system 101.

FIG. 1 also shows that the data processing system 101 includes a memory 107 and one or more processors 102. The memory 107 includes the CSPAN Engine 110 which is preferably implemented as instructions stored in memory 107 and executable by processor 102.

FIG. 1 also includes a computer readable storing medium 103 for storing the CSPAN Engine 110. FIG. 1 also includes one or more input/output devices 104 that allow data to be input and output to and from the data processing system 101. It will be understood that embodiments of the data processing system 101 also include standard software components such as operating systems and the like and further include standard hardware components not shown in the figure for clarity of example.

Figure 2:
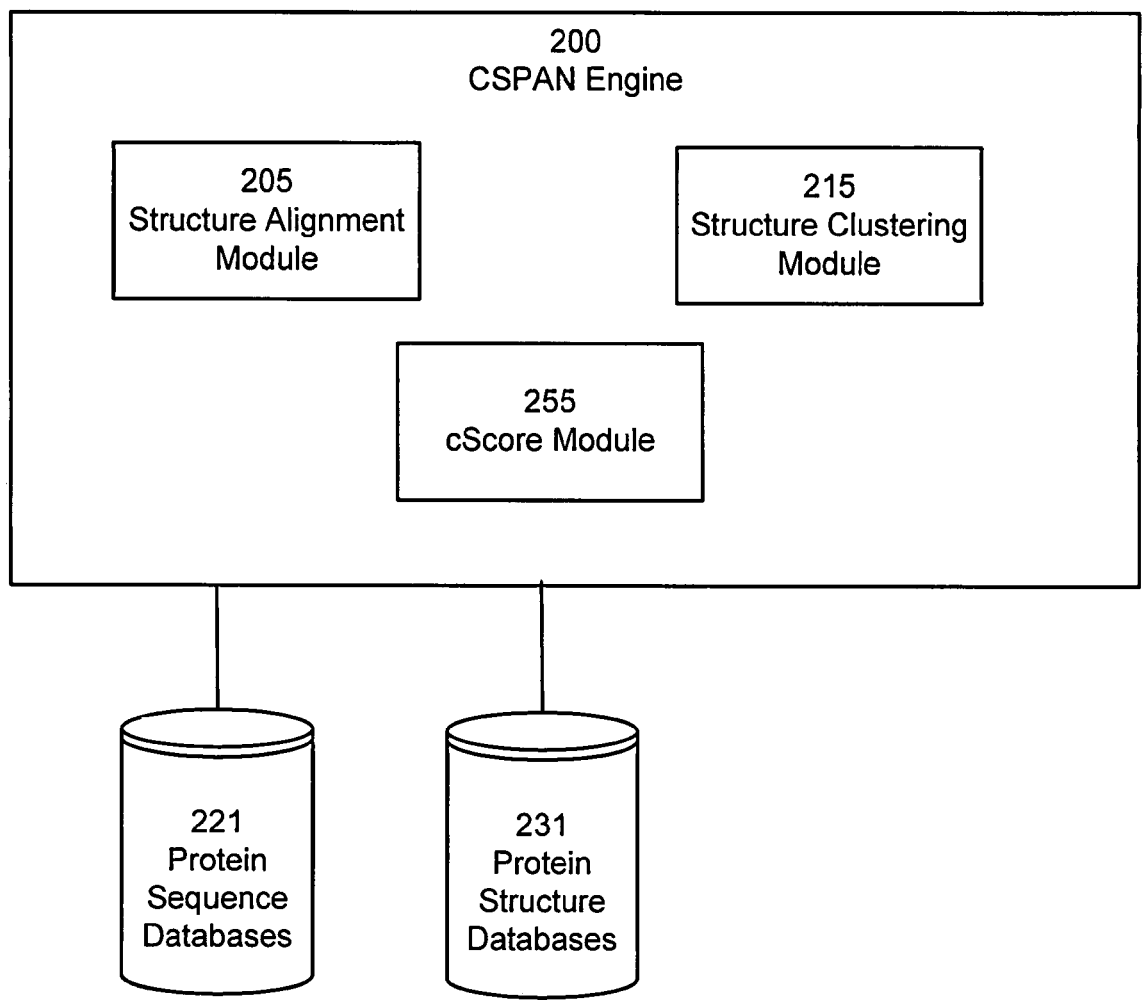
FIG. 2 illustrates the CSPAN engine according to one embodiment.

FIG. 2 illustrates one embodiment of the CSPAN Engine 200. The CSPAN Engine functions to generate conservation scores for residues in spans of protein structures identified based on a family of protein structures. The CSPAN Engine 200 is adapted to import protein structures from Protein Structure Databases 231 such as Protein Data Bank (PDB, available at the website of the Research Collaboratory for Structural Bioinformatics). The CSPAN Engine 200 is adapted to communicate with Protein Sequence Databases 221 such as MvirDB (Zhou et al. NAR) or GenBank (available at the website of the National Center for Biotechnology Information).

The CSPAN Engine 200 consists of three modules, a Structure Alignment Module 205, a Structure Clustering Module 215 and a Conservation Score Module 255. The functions of the engines discussed herein are separated into modules for purposes of discussion only. Different embodiments of the present invention may distribute functions among modules in different ways.

Protein Structure Alignment

The Structure Alignment Module 205 functions to generate protein structure alignments between protein structures. Methods of solving protein structure are discussed below in the section titled Protein Structure Modeling. The Structure Alignment Module 205 takes as input a set of protein structures identified for clustering. The set of protein structures may be identified by user input or as output of another program. The Structure Alignment Module 205 is adapted to import protein structures directly from the Protein Structure Databases.

The Structure Alignment Module 205 generates protein structure alignments by determining the optimal residue-residue correspondence between protein structures. The optimal residue-residue correspondence is computed by computationally aligning or superimposing the sets of spatial co-ordinates defining points representing each residue (e.g. alpha carbon (Calpha) atoms) that form the protein structures to minimize distance between the spatial co-ordinates of the sets of atoms. Typically, the sets of spatial-coordinates represent the alpha carbon backbone of the two protein structures but structure alignments may also incorporate spatial co-ordinates of other atoms such as side chain atoms or other sets of spatial co-ordinates representing each residue.

According to one embodiment of the present invention, the Structure Alignment Module 205 uses a variety of methods and metrics for generating an optimal set of correspondences. The Structure Alignment Module 205 calculates the root mean square deviation (RMSD) of all the corresponding alpha carbon atoms in the backbone. The Structure Alignment Module 205 further calculates the number of equivalent or structurally aligned residues.

In some embodiments, the Structure Alignment Module 205 calculates distance matrices such as GDT matrices in order to generate an optimal set of correspondences. Alternatively, the Structure Alignment Module 205 generates the optimal set of correspondences by maximizing the number of equivalent residues while RMSD is kept close to a constant value.

In the generation of the set of correspondences, various cutoff values can be specified to increase or decrease the stringency of the alignment or super-position. These cutoffs can be specified using distance in Angstroms. Depending on the level of stringency employed in the present invention, the distance cutoff used is selected from a range of 0.5 to 10.0 Angstroms. In a specific embodiment, the cutoff may have default value of 5.0 Angstroms. One of ordinary skill will recognize that the utility of stringency criterion depends on the resolution of the structure determination.

In another embodiment of the present invention, the Structure Alignment Module 205 generates the set of residue-residue correspondences using a local-global alignment (LGA), as described in US Patent Application Number 2004/0185486. In this method, a set of local superpositions are created in order to detect regions of the protein structures that are most similar.

LGA uses the LGA_S scoring function to determine local and global similarity in determining the optimal superposition or alignment between two protein structures. The LGA_S scoring function has two metrics, LCS (longest continuous segments) and GDT (global distance test), defined for the detection of regions of local and global structure similarities between analyzed structures. In comparing two protein structures (e.g., M-model and T-target), the LCS procedure localizes and superimposes the longest segments of residues that can fit under a selected set of RMSD cutoffs. The GDT algorithm is designed to complement evaluations made with LCS searching for the largest (not necessary continuous) set of "equivalent" residues that deviate by no more than specified distance cutoff.

Let:
m—the number of residues in M structure,
t—the number of residues in T structure,
R(r)=100/t*L(r), where L(r) is the length of the identified longest continuous segment of M:T residue pairs that fits under r Å of RMSD cutoff,
X—the set of all M:T superpositions calculated by LGA algorithm,
G(s, d)—the number of M:T residue pairs for which the distance between Calpha (Alpha carbon) atoms is not greater than d Å after the superposition s∈X is applied,
D(d)=100/t*max{G(s,d):s∈X} is the maximal detected percentage of the Ca atoms in T structure that are within a distance threshold of d Å from M structure upon calculated s∈X superpositions.

The LGA_S structure similarity scoring function is defined as a function of two structures. M and T calculated as a combination of R(r) results from LCS calculations using the set of n RMSD cutoffs r (e.g., n=3; r=1.0, 2.0, 5.0), and D(d) results from GDT calculations using the set of k distance cutoffs d (e.g., k=20; d=0.5, 1.0, . . . , 10.0)

$$LGA\_S(M, T) = (1 - w) * S(LCS(M, T)) + w * S(GDT(M, T)),$$

where $$S(LCS) = \frac{2}{n \cdot (n+1)} \sum_{j=1}^{n} (n - j + 1) * R(r_j), n = 3, r_j = 1.0, 2.0, 5.0,$$

-continued $$S(GDT) = \frac{2}{k \cdot (k+1)} \sum_{j=1}^{k} (k-j+1) * D(d_j), k = 20, d_j = 0.5, 1.0, \ldots, 10.0,$$

and w=0.75 is a parameter (0<=w<=1) representing a weighting factor between LCS and GDT results.

STRALCP

Figure 3:
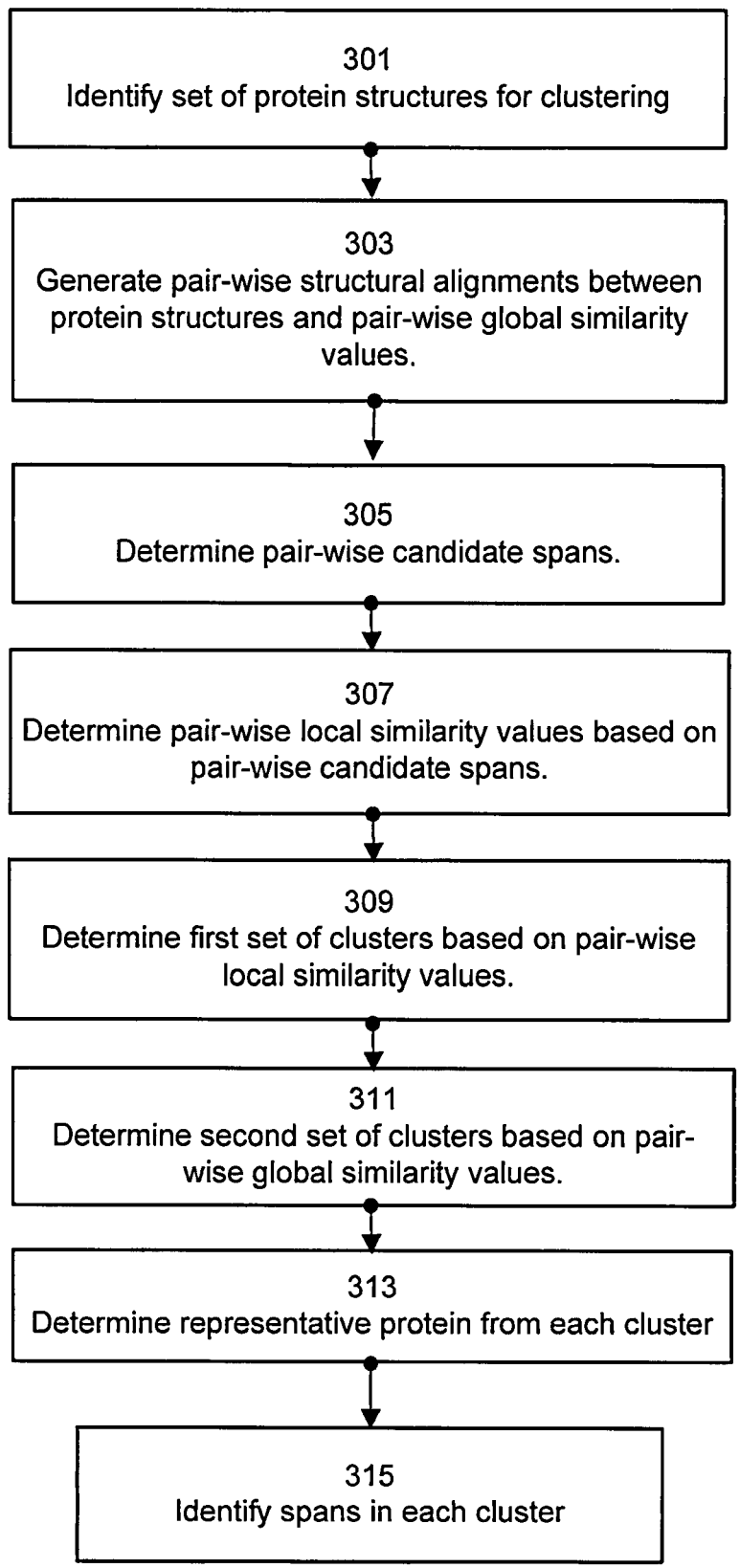
FIG. 3 illustrates a high level workflow of the STRALCP protein structure clustering method according to one embodiment.

FIG. 3 illustrates a high level overview of protein structure clustering using the CSPAN Engine 200. The Structure Alignment Module 205 initially identifies 301 a set of proteins for clustering. According to this embodiment, the set of protein structures may be specified by the user or may be selected based on any criteria such as homology or annotation in a protein sequence database.

The Structure Alignment Module 205 generates 303 pair-wise structure alignments between the identified protein structures. In one embodiment, the Structure Alignment Module 205 uses the above described Local Global Alignment (LGA) program to generate 303 the pair-wise structural alignment between all identified protein structures. Other embodiments may employ different methods of generating a global alignment, a local alignment or any combination thereof. In embodiments in which a global alignment is generated, a maximum distance between residues in the structural alignment is a specified. This distance ranges from 0.5 to 10.0 Angstroms. In a specific embodiment, the pre-determined distance is set to a default value of 5.0 Angstroms.

The Structure Clustering Module 215 determines 305 pair-wise candidate spans of contiguous residues based on the generated pair-wise structural alignment. A span is defined as a contiguous plurality of pairs of residues from two protein structures whose alpha carbon co-ordinates (or any other set of spatial co-ordinates used to represent each residue) are within a pre-determined distance from each other in the structure alignment.

The Structure Clustering Module 215 determines 305 pair-wise candidate spans based on a threshold length of contiguous residues such as 3, 4, 5, or 6 contiguous residues. According to the embodiment, the Structure Clustering Module 215 determines 305 the pair-wise candidate spans based on a pre-determined distance between corresponding residues in a local alignment calculated using root mean square deviation in a local window of residues. According to the embodiment, the pre-determined distance may be calculated using a root mean square deviation based on different sized windows surrounding a given pair of residues in the pair-wise protein structure alignment, for instance windows of 3, 4, 5 or 6 residues. Those skilled in the art will note the utility in adjusting threshold parameters for both the length and the threshold distance between residues in determining candidate spans.

In a specific embodiment, the Structure Clustering Module 215 determines 305 pair-wise candidate spans of at least 5 contiguous residues in the pair-wise structure alignment that are superimposed in a global alignment within a distance cutoff of 5.0 Angstroms, and locally with RMSD cutoff of 0.5 Angstroms. The RMSD between individual residues is calculated using a 3-residue-long window.

The Structure Clustering Module 215 determines 307 a plurality of pair-wise local similarity values based on the pair-wise candidate spans. In one embodiment, pair-wise local similarity values are based on a set of fragments that are determined for each structure. The Structure Clustering Module determines a set of fragments for each protein structure, each fragment including a set of residues that are contiguous in the polypeptide associated with the protein structure. In one embodiment, the set includes sequential fragments defined by splitting the corresponding amino-acid sequence into consecutive n-residue-long sub-sequences. In a specific embodiment, the number of contiguous residues is 10 (i.e. n=10 and a 120-residue-long protein comprises 12 fragments).

The Structure Clustering Module 215 determines 307 a plurality of pair-wise local similarity values, which indicate whether two pair-wise fragments between two protein structures share a candidate span. Each fragment that does not share a span with a protein structure in a pair-wise comparison is referred to as an "empty fragment." According to the embodiment, the pair-wise local similarity values can be represented in different ways. In one embodiment, the pair-wise local similarity values can be represented as binary or absolute value indicating whether or not a pair of fragments share a candidate span or are empty fragments (e.g. 1 for a shared span, 0 for an empty fragment). Alternatively, the pair-wise local similarity value may be represented as a numeric value indicating the number of residue pairs within two fragments that are in one or more candidate spans. The numeric value can be a number of residue pairs within two fragments that are in a candidate span or a percentage of the residues in the fragments that form residue pairs in a candidate span. Empty fragments would be assigned a value of nil or zero.

The Structure Clustering Module 215 determines 309 a set of clusters based on the pair-wise local similarity values. In a specific embodiment, a list of protein structures having at least a pre-determined number of fragments having pair-wise local similarity values indicating that fragments share a set of spans is generated. In a specific embodiment, the list of protein structures is limited to protein structures for which 80% of the fragments in both protein structures share a span or are "non-empty." The Structure Clustering Module 215 uses the lists of non-empty fragments to determine 309 an initial maximal cluster of protein structures wherein each pair of protein structures have 80% of their fragments share a candidate span (i.e. are non-empty).

The Structure Cluster Module 215 determines 311 a second set of clusters based on the pair-wise global similarity values between protein structures. Pair-wise global similarity values are generated as part of the structural alignment to represent the overall or global similarity between the alpha carbon backbones of two protein structures. According to the embodiment, pair-wise global similarity values can be any suitable value to measure the overall similarity between proteins, such as root mean square deviation (RMSD) or global distance test (GDT). Other appropriate values to measure global similarity will be apparent to those skilled in the art. In embodiments in which LGA is used to determine structural alignment, LGA_S values are calculated as pair-wise global similarity values.

In determining 311 the second set of clusters, the Structure Cluster Module 215 uses the global pair-wise similarity values to determine that the clusters of proteins from the initial clustering have good pair-wise global similarity values. In one embodiment, the Structure Cluster Module identifies pair-wise global similarity values between protein structures in a cluster and reassigns protein structures to different clusters if the pair-wise similarity values between a pair of the protein-structures is below a certain value. In a specific embodiment, the Structure Cluster Module 215 uses a cutoff of 60% global similarity based on an LGA_S score.

In re-assigning the protein structures to different clusters to determine 311 the second set of clusters based on the pair-wise global similarity values, the Structure Cluster Module 215 seeks to minimize the number of clusters necessary to assign each protein structure in the identified set of protein structures to a cluster. According to the embodiment, the Structure Cluster Module 215 is provided values specifying a pre-determined minimum and maximum number of clusters to form, the values ranging from one cluster to the number of given protein structures. According to the embodiment, the resulting number of clusters is determined by the Structure Cluster Module 215 as a minimum number of clusters needed to distribute all given protein structures and satisfy the threshold values of percentage of non-empty fragments and global alignment values.

The Structure Cluster Module 215 determines 313 a representative protein structure from each cluster. The representative protein structure is the protein structure that has the highest local and global similarity to each other protein structures in the cluster as defined by the pair-wise local similarity values. The Structure Cluster Module 215 generates for each protein structure in a cluster, a list of all pair-wise local and global similarity values. The Structure Cluster Module 215 selects the protein structure in each cluster that has the highest pair-wise local and global similarity values as the representative structure. According to the embodiment, the pair-wise local and global similarity values may be assigned different weighting schemes in calculating the representative cluster. Those skilled in the art will readily note the utility in different weighting schemes. In a specific embodiment, the protein structure that has the largest number of non-empty fragments, the highest LGA_S value with other members of the cluster, and the highest number of residues in calculated spans is selected as the representative protein structure.

The Structure Cluster Module 215 then identifies 315 a set of spans for each identified cluster based at least in part on the plurality of pair-wise candidate spans. For each identified cluster, pair-wise candidate spans are combined to form common spans of the set of residues which are conserved between all structures within the cluster or family of protein structures. The Structure Cluster Module 215 may identify 315 spans by performing another structural alignment such as a Local Global Alignment or by combining the correspondences generated in the pair-wise structural alignments. The degree of structural homology may differ between different pairs of protein structures within a cluster. Therefore, not all pair-wise candidate spans are necessarily incorporated into the representative set of spans for each given cluster.

Once the clustering has been completed and representative protein structures have been selected, the set of representative protein structures are used to assign newly-solved protein structures to respective clusters. In one embodiment, the Structure Alignment Module 205 performs a structural alignment between newly-solved protein structure and each representative protein structure for each cluster. The structural alignment may be a global alignment, a local alignment or any combination thereof. The Structure Clustering Module 215 generates a pair-wise local similarity value, a pair-wise global similarity value or any suitable similarity value to compare the newly-solved protein structure to each representative protein structure for each cluster. Other suitable similarity values for comparing the newly-solved protein structure to each representative structure will be readily recognized by those skilled in the art.

The Structure Clustering Module 215 then assigns a protein structure to one of the clusters based on the generated similarity values. For example, the newly-solved protein structure will be assigned to the cluster for which it has the highest similarity value in comparison to the representative protein structure. According to the embodiment, the Structure Clustering Module 215 may use one or more threshold similarity values in assigning the protein structure to a cluster in order to ensure that similarity values are above a threshold similarity before assigning a protein structure to a cluster. In a specific embodiment, a minimum global similarity value of 60% is used. Other embodiments may include the use of pair-wise local similarity values that indicate whether fragments generated for a newly-solved protein structure and each representative protein structure contain candidate spans as discussed with respect to step 307.

Conservation Score

The cScore Module 255 generates scores representative of the structural conservation of the residues within a cluster or family of protein structures for each of the residues within a span.

A scoring function maps an abstract concept to a numeric value. Conservation scores are generated to assign a quantitative value to the degree of evolutionary conservation of a residue at a position in the sequence. Evolutionary conservation is defined by the phenomena in which residues at a position in a molecule are not subject to deletion or substitution in molecules within a species or homologous molecules across different species. It is inferred from conservation that the residue is integral to the function of the molecule and a substitution would cause a loss-of-function in the molecule, potentially rendering unviable the organism producing the molecule. Therefore, conservation is used as a measure of the relative functional importance of a residue.

In the present invention, the cScore Module 255 generates a score representative of structural conservation for each of the residues within a span, herein referred to as a "cScore". In the scoring of conservation, various similarity metrics may be employed. Suitable similarity metrics are discussed in detail in the section below titled Similarity Metrics.

The cScore Module 255 calculates a consensus residue for a position in the span or correspondence between all protein structures from a cluster. The consensus residue is calculated based on the residue most frequently found in the aligned cluster or family protein structures at a position in the correspondence. Scores for residues in every target sequence are generated by comparison to the consensus residue, the comparison being made using the selected similarity metric. Scores for residues in each target sequence can then combined into a single conservation score or cScore by averaging the score for each residue in the target sequences.

Those skilled in the art will readily recognize the utility and possibilities inherent in combining the cScores with other scoring functions and values. In some embodiments the cScore Module 255 combine cScores with scores representative of residue frequency in a database of values. By combining cScores with residue frequency values, a user can add extra information regarding the relative uniqueness of a residue based on local sequence context. In some embodiments this residue frequency is based on the local sequence context of the residue as described in co-owned application Ser. No. 11/735,981 titled Structure Based Analysis for Identification of Protein Signatures: pScore, filed on Apr. 16, 2007, incorporated herein by reference. The cScore Module 255 may also combine cScores with scores indicative of the probability a residue resides on the surface of the ternary or quaternary structure of a protein. This added information aids in finding residues that are surface exposed and amenable to binding by small molecule ligands or antibodies. It is well known to those of ordinary skill in the art how to assign a probability associated with the likelihood that a residue is a surface residue. Examples of ways to obtain such probabilities include, e.g., computational algorithms such as those implemented in PredictProtein (Rost and Liu, 2003). Another method of predicting surface accessible residues incorporates the use or creation a three dimensional model of the protein structure.

In some embodiments, the cScore Module 255 weights the cScores by the number of protein structures in the cluster before or during the combining of the two scores. The use of alternate methods of weighting and normalization based on the number of sequences will be apparent to those skilled in the art.

The cScore module 255 also generates distributions of the cScores generated for a given span or all spans in a cluster or family of proteins. The generation of cScore distributions provides many uses for subsequent analyses and summary reports. Examples of such distributions include but are not limited to frequency distributions or probability distributions. In one application of the present invention, percentile cutoffs are employed as a method of selecting residues from the distribution for further analyses. In other embodiments, the cScores are "binned" or discretized for further analyses based on this distribution. In other embodiments, the cScore Module 255 stores distribution profiles for subsequent analyses.

Signature Identification

According to certain embodiments of the present invention, the calculation of cScores provides information used in the identification of a subset of residues which form a protein signature.

In some embodiments of the present invention, the cScore Module 255 displays cScores onto a three dimensional representation of a polypeptide to identify a set of high scoring residues on the surface of the protein which are proximate in three dimensional space. This display is used to identify a set of residues which define a protein signature. This set can contain any number of residues but in most embodiments will be two or more residues, such as, e.g., two three, four, five, six, seven, eight, nine, ten, or more residues. In alternate embodiments, high scoring values with residues proximate in three dimensional space can identified computationally.

In one embodiment, only scores above or below a certain value are displayed on the protein. In another embodiment, residues are colored according to score. In another embodiment, these scores are displayed along with other scores representative of other data such as residue frequency in a database of sequence.

According to the application of the present invention, various programs for rendering the three dimensional display of a protein from a set of atom coordinates are employed in this method. RasMol is a common program for molecular graphics visualization. Other programs used to visualize three dimensional protein structures are Chime and Protein Explorer.

In another embodiment, the cScore Module 255 projects cScores onto a linear representation of the two-dimensional amino acid sequence in order to identify signatures of residues contiguous in linear sequence. In alternate embodiments, stretches of contiguous residues satisfying set scoring criteria are identified programmatically.

In one embodiment, the cScore Module 255 are displays cScores as a line graph where the amino acid sequence is plotted along the x-axis and the numeric values of the cScores are displayed on the y-axis. The scores can also be displayed on the y-axis along with other scores including, but not limited to, scores representative of residue frequency in local sequence context. In some embodiments, the cScores can be represented by coloring the residues in the correspondence or by other visualization techniques.

Similarity Metrics

Various similarity metrics are used to score the uniqueness or conservation of the residues in a correspondence. These metrics include but are not limited to a trinary system or substitutions matrices. It is expected that those skilled in the art can envision a variety of comparable similarity metrics for calculating conservation and uniqueness.

In one embodiment of the present invention, the similarity metric is based on trinary system of residue identity, non-identity and similarity. Residues from each sequence in a correspondence are compared with the corresponding residue in the reference protein. Alternately, residues from each sequence are compared with a consensus residue identified in the majority of the sequences in set of the correspondences. Residue identity refers to the residue comprising the same amino acid as the residue to which it is compared. Residue similarity refers to the two residues under comparison being part of a pre-defined group or family with similar features. If two residues are neither identical nor similar, the residues are non-identical. Scores of 1, 0 and 0.5 are assigned based on identity, non-identity and similarity respectively. It is expected that those skilled in the art can imagine a variety of different scoring techniques.

Various pre-defined groupings used to specify may be employed in this technique. Amino acids are referred to herein by corresponding single letter symbols as defined by IUPAC (International Union of Pure and Applied Chemistry), a table listing amino acids and their corresponding single letter symbols may be found in a standard biochemistry textbook, for example, Leningher, Principles of Biochemistry, W H Freeman & Co (2004). One method of grouping the 20 known amino acids is by chemistry and size: aliphatic (AGILPV), aromatic (FWY), acidic (DE), basic (RKH), small hydroxylic (ST), sulfur-containing (CM) and amidic (NQ).

Other grouping schemes are based on functional properties such as: acidic (DE); basic (RKH); hydrophobic non polar (AILMFPWV); and polar uncharged (NCQGSTY). An example of a grouping scheme based on the charge of amino acid is: acidic (DE); basic (RKH) and neutral (AILMFPWV NCQGSTY). A grouping scheme based on structural properties of amino acids is: ambivalent (ACGPSTWY); external (RNDQEHK); internal (ILMFV) (Karlin and Ghandour, 1985). Other grouping schemes based on physical properties such as codon degeneracy or kinetic properties can also be employed.

In an alternate embodiment, substitution matrices may be used to calculate the similarity metric. Substitution matrices represent to the rate at which each possible residue in a sequence changes to each other residue over time. Substitution matrices are 20 by 20 matrices containing preferred substitutions propensity for all possible pairs of amino acids. The preferred substitution propensities may be calculated based on a set of homologous sequences or many sets of homologous sequences. Two substitution matrices for amino acids commonly used in the art are PAM (Point Accepted Mutation) and BLOSUM (BLOck SUbstitution Matrix). Substitution matrices may also be used to create a grouping such as above by identifying the grouping of amino acids which minimizes the off diagonal elements in the substitution matrix (Fygenson et al., 2004).

WORKING EXAMPLE 1

HIV-1 Protease

In a first working example, conservation was scored for the protein structure of the protease of HIV-1 complexed with a dihydroethylene-containing inhibitor (PDB structure: 1hiv chain A) relative to a computationally identified cluster or family of related protein structures.

Figure 4:
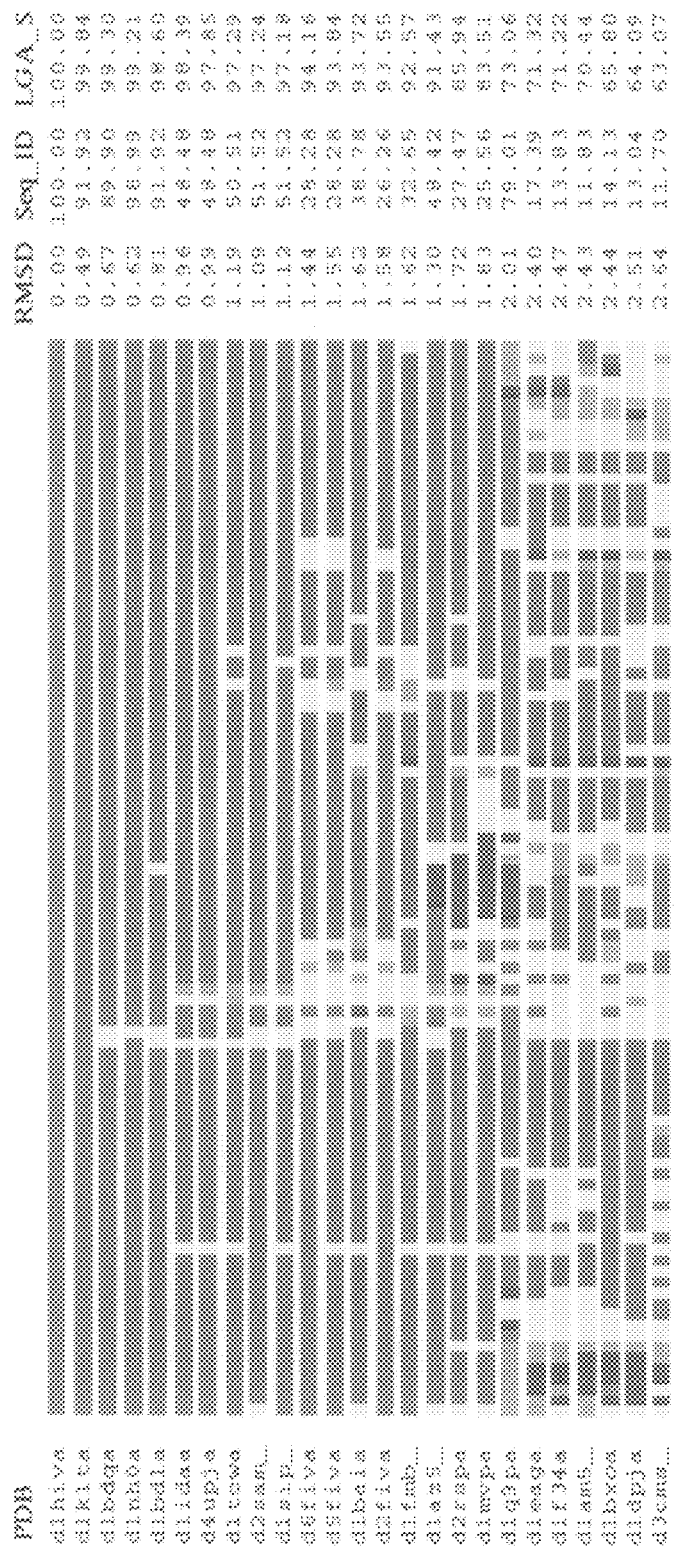
FIG. 4 illustrates a local global alignment of 25 representative structures from SCOP fold "b.50" using the protein structure of HIV-1 protease as a frame of reference.

A local global alignment of 110 protein structures from the SCOP (Structural Classification Of Proteins) fold "b.50" and HIV-1 protease was preformed using LGA. FIG. 4 illustrates a portion of this local global alignment using 25 representative structures from SCOP fold "b.50" and the protein structure of HIV-1 protease as a frame of reference. In FIG. 4, colored bars represent the Calpha-Calpha distance deviation between the superimposed protein structures and HIV-1 protease protein structure (1hiv_A). Each bar represents protein structure residues from the N terminal (left) to the C terminal (right). Residue pairs superimposed with a distance below 2 Angstroms are colored green. Residues pairs superimposed with a distance below 4 Angstroms are colored in yellow. Residues superimposed below 6 Angstroms in orange, and residues at or above 6.0 Å in red. Terminal residues that were not aligned are colored in grey. Calculated global levels of sequence identity (Seq_ID) and structure similarity (LGA_S) between proteins from PDB and 1hiv_A are given in the right columns. The top 19 structures below HIV-1 protease protein structure in the bar diagram belong to the protein structure family b.50.1.1. The bottom six structures in the bar diagram belong to the family b.50.1.2. As illustrated in the alignment, the structures from family b.50.1.1. provided better alignments with the HIV-1 protease protein structure than the structures from family b.50.1.2.

Figure 5:
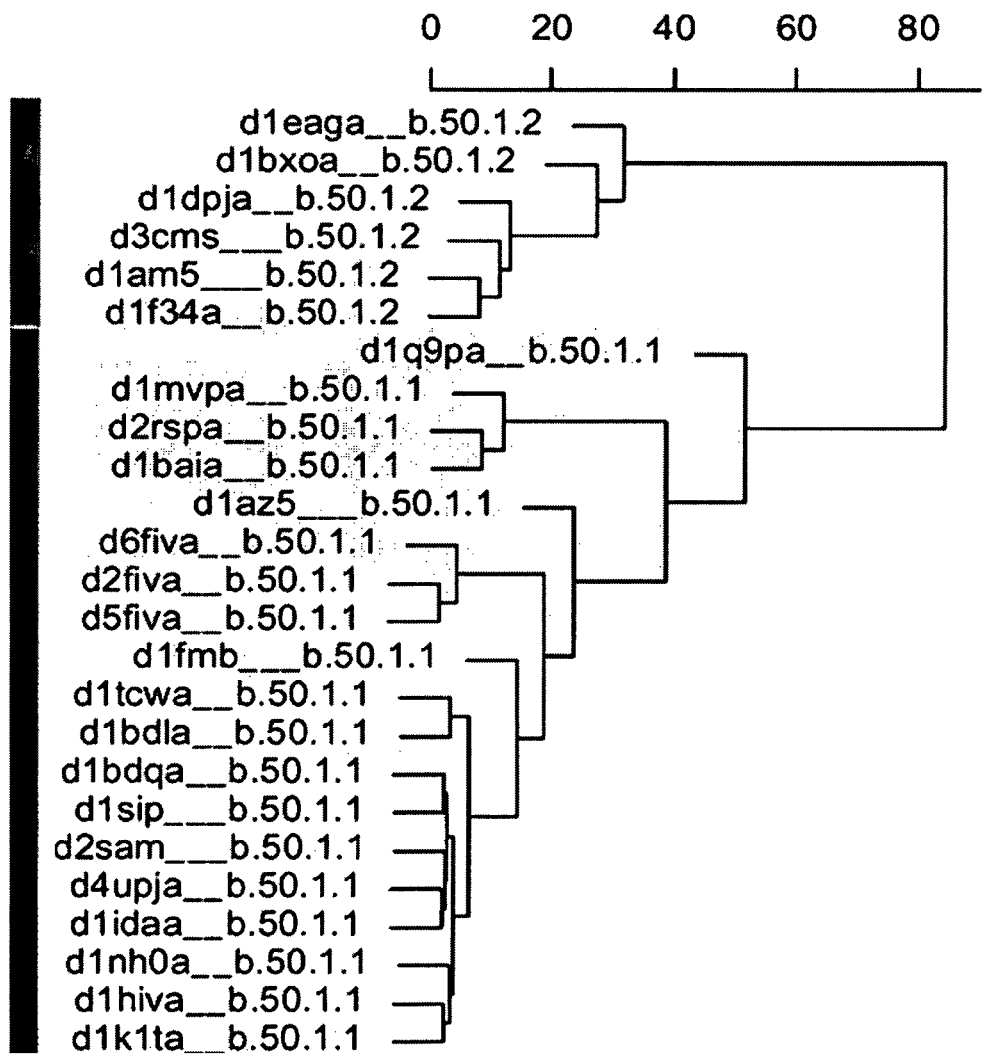
FIG. 5 illustrates a clustering of the HIV-1 protease protein structure with the 25 representative protein structures from SCOP fold b.50.
Figure 7:
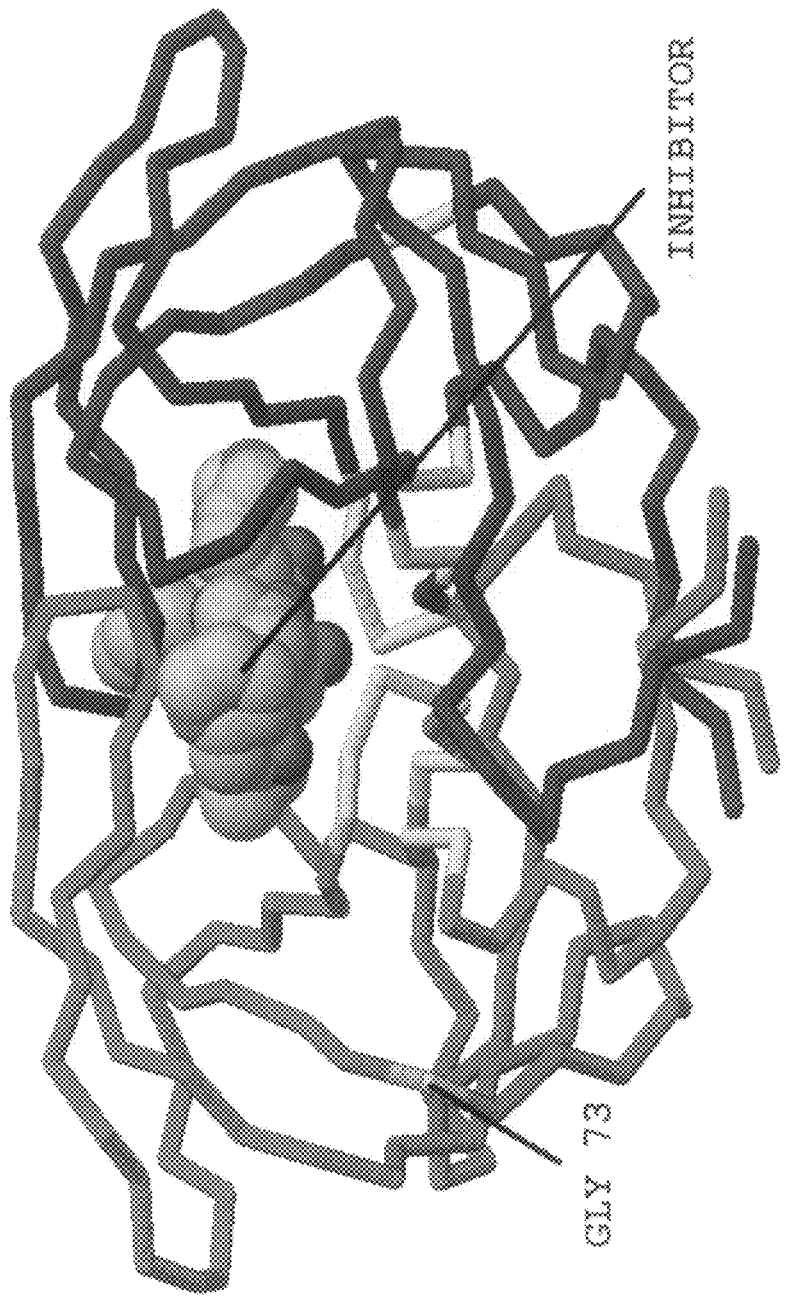
FIG. 7 illustrates the HIV-1 protease homodimer complexed with a dihydroethylene-containing inhibitor (PDB entry 1hiv chain A) as a reference protein upon which span residues with high cScores are projected.
Figure 8:
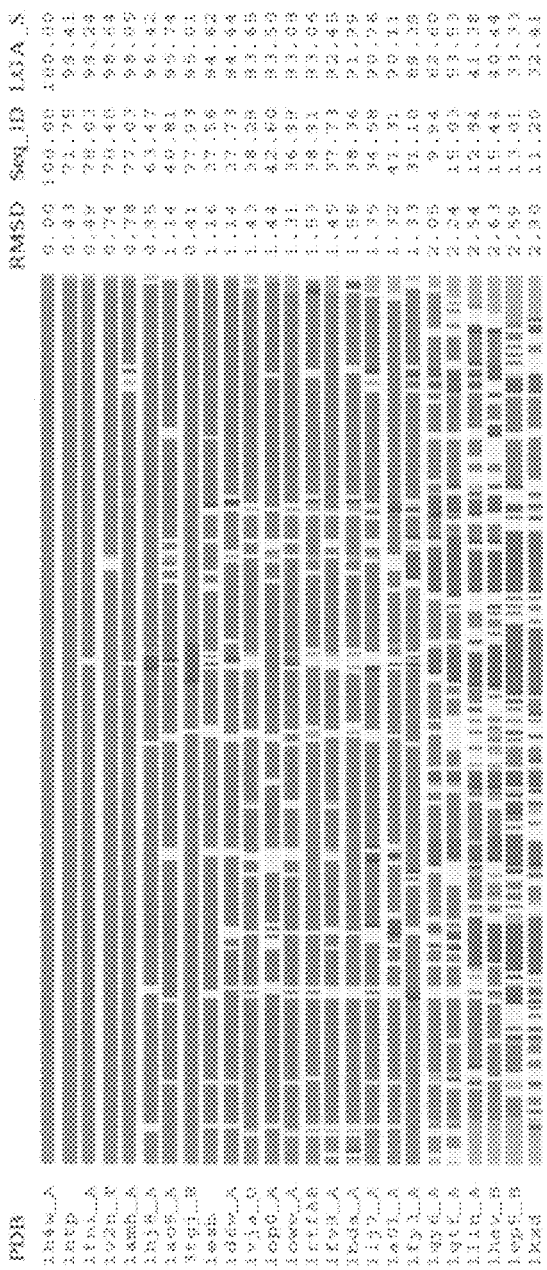
FIG. 8 illustrates local global structural alignment 25 representative protein structures from SCOP fold b.47 using the protein structure of human trypsin IV as a reference protein structure.
Figure 9:
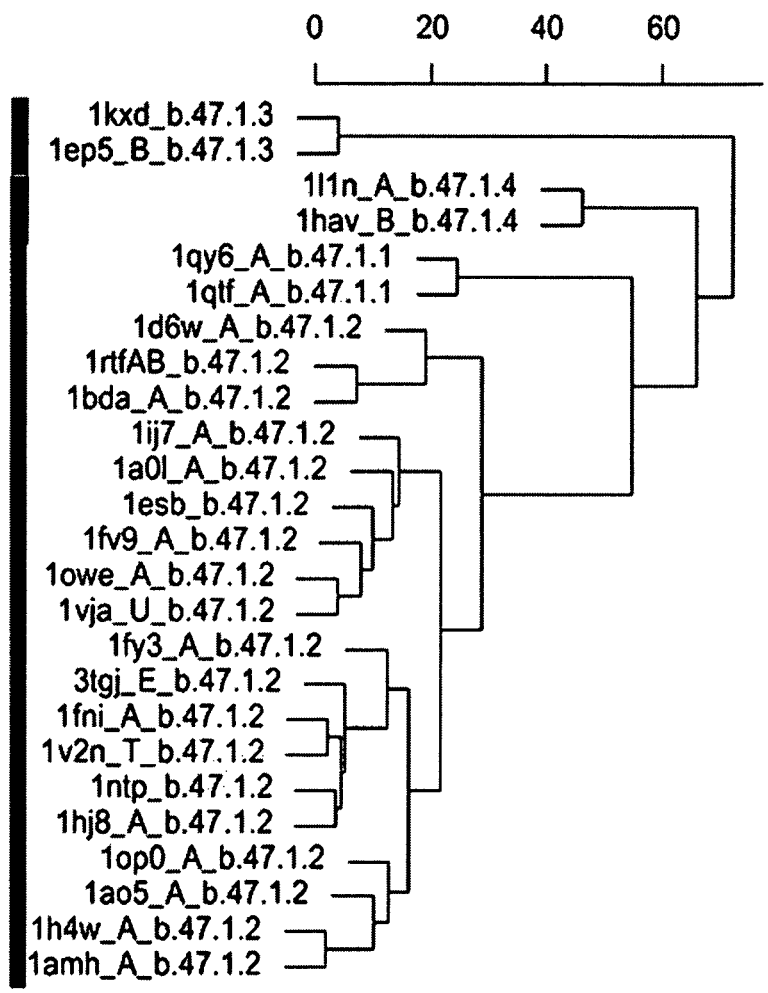
FIG. 9 illustrates a clustering of the protein structure of human trypsin IV with 25 protein structures from SCOP fold b.47.

FIG. 5 illustrates a clustering of the HIV-1 protease protein structure with the 25 representative protein structures from SCOP fold b.50. Using the STRALCP approach outlined with respect to FIG. 3, each of the 110 structural domains was computationally clustered into either of two clusters. The protein structure of HIV-1 protease was clustered within cluster #1 together with 70 structures from SCOP family b.50.1.1. FIG. 5 illustrates the portion of cluster #1 with the HIV-1 protease protein structure (marked as d1hiva) clustered with 19 protein structures from family b.50.1.1. Cluster #1 corresponds to the blue colored bar in FIG. 5. Cluster #1 corresponded precisely to the SCOP families of retroviral proteases (Retropepsins; SCOP family b.50.1.1, with 406 domains) and the pepsin-like proteins (SCOP family b.50.1.2, with 160 domains).

The STRALCP algorithm was run with the following default parameters Candidate spans of a minimum of 5 contiguous residues were identified from each pair-wise structural alignment using a pre-determined distance of 0.5 Angstroms of calculated root mean square deviations using a window size of 3 residues. Sequential fragments 10 residues in length were determined for each protein structure from fold a. 8. Pair-wise local similarity values indicating whether pairs of fragments shared candidate spans were calculated. An initial clustering was performed using a cutoff value of 80% non-empty fragments between each protein structure in each cluster. A second and final clustering was performed by applying a cutoff value of 60% global structure similarity to LGA_S scores generated for the pair-wise structural alignments.

Figure 6:
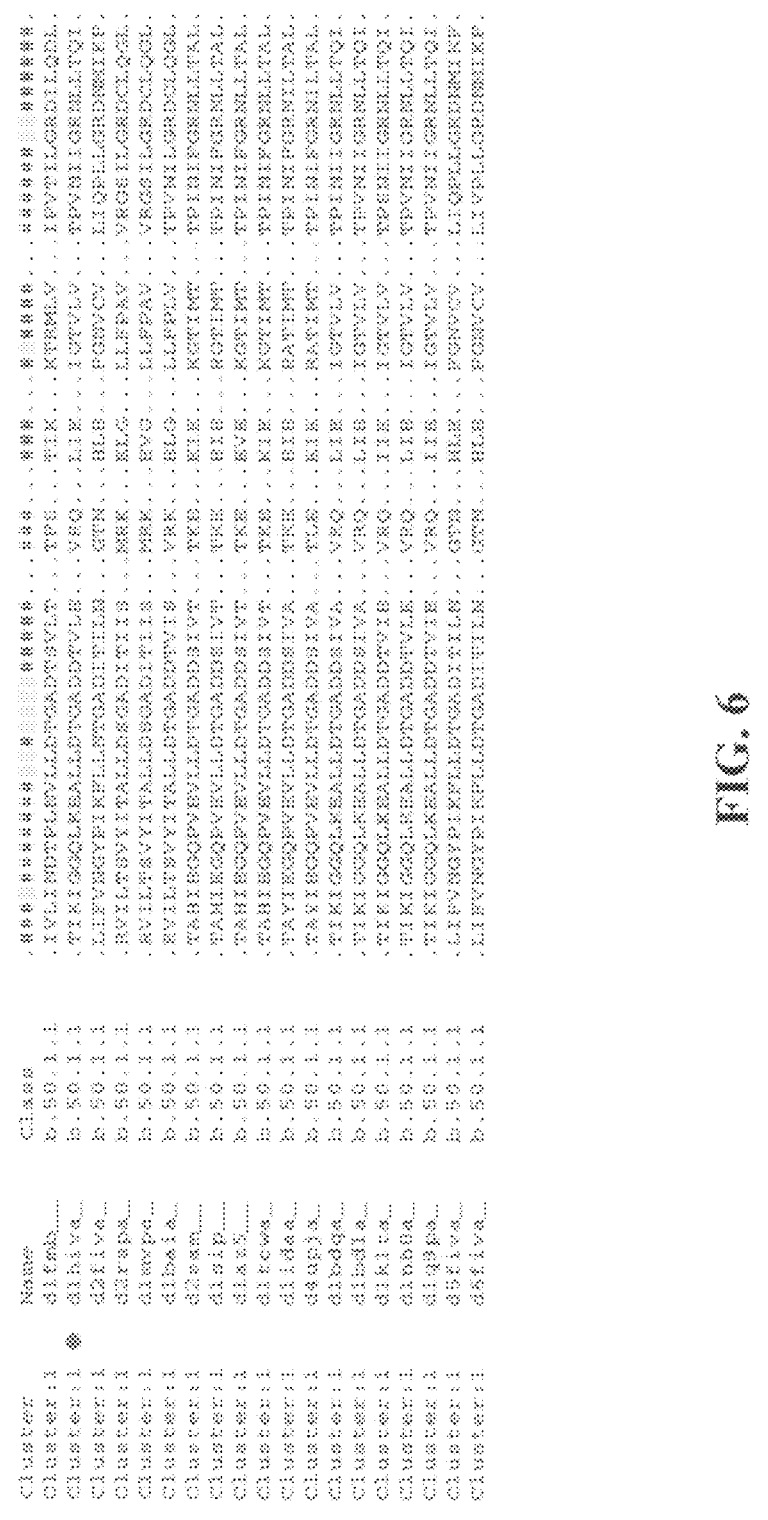

FIG. 6 illustrates a multiple sequence structure alignment of cluster #1 showing the "spans" or locally aligned regions in cluster #1. Each row begins from the cluster number, followed by the domain name, and the set of amino-acids that are extracted from detected structurally conserved spans. Dots indicate regions that structurally deviate in at least one pair-wise comparison between members of the cluster. For purposes of illustration, only 19 of the 70 structures in cluster #1 are shown here. FIG. 6 lists sequences with the following SEQ ID NOs. For the sequence ".IVLINDTPLNVLLDT-GADTSVLT . . . TFS . . . TIK . . . KTRMLV . . . IPVTILGRDILQDL." with the name "d1fmb_", "IVLINDT-PLNVLLDTGADTSVLT" is SEQ ID NO:1, "KTRMLV" is SEQ ID NO:2, and "IPVTILGRDILQDL" is SEQ ID NO:3. For the sequence ".TIKIGGQLKEALLDTGADDTVLE . . . VRQ . . . LIE . . . IGTVLV . . . TPVNIIGRNLLTQI." named "d1hiva_", "TIKIGGQLKEALLDTGADDTVLE" is SEQ ID NO:4, "IGTVLV" is SEQ ID NO:5, "TPVNIIGRN-LLTQI" is SEQ ID NO:6. For the sequence ".LIFVNGYP-IKFLLNTGADITILN . . . GTN . . . HLE . . . FGNVCV . . . LIQPLLGRDNMIKF." named "d2fiva_", "LIFVNGYPIK-FLLNTGADITILN" is SEQ ID NO:7, "FGNVCV" is SEQ ID NO:8, and "LIQPLLGRDNMIKF" is SEQ ID NO:9. For the sequence ".RVILTSVYITALLDSGADITIIS . . . MRK . . . ELG . . . LLFPAV . . . VRGSILGRDCLQGL." named "d2repa_", "RVILTSVYITALLDSGADITIIS" is SEQ ID NO:10, "LLFPAV" is SEQ ID NO:11, and "VRGSILGRD-CLQGL" is SEQ ID NO:12. For the sequence ".RVILTSVYI-TALLDSGADITIIS . . . MRK . . . EVG . . . LLFPAV . . . VRGSILGRDCLQGL." named "d1mvpa_", "RVILTSVYI-TALLDSGADITIIS" is SEQ ID NO:13, "LLFPAV" is SEQ ID NO:14, and "VRGSILGRDCLQGL" is SEQ ID NO:15. For the sequence ".RVILTSVYITALLDTGADDTVIS . . . VRX . . . ELG . . . LLFPLV . . . TPVNILGRDCLQGL." named d1baia_", "RVILTSVYITALLDTGADDTVIS" is SEQ ID NO:16, "LLFPLV" is SEQ ID NO:17, and "TPV-NILGRDCLQGL" is SEQ ID NO:18. For the sequence ".TAHIEGQPVEVLLDTGADDSIVT . . . TKE . . . EIE . . . KGTIMT . . . TPINIFGRNLLTAL." named "d2sam_", "TAHIEGQPVEVLLDTGADDSIVT" is SEQ ID NO:19, "KGTIMT" is SEQ ID NO:20, and "TPINIFGRNLLTAL" is SEQ ID NO:21. For the sequence ".TAHIEGQPVEVLLDT-GADDSIVT . . . TKE . . . EIE . . . RGTIMT . . . TPINIFGRN-LLTAL." named "d1sip_", "TAHIEGQPVEVLLDT-GADDSIVT" is SEQ ID NO:22, "RGTIMT" is SEQ ID NO:23 and "TPINIFGRNLLTAL" is SEQ ID NO:24. For the sequence ".TAHIEGQPVEVLLDTGADDSIVT . . . TKE . . . EVE . . . KGTIMT . . . TPINIFGRNLLTAL." named "d1az5_", "TAHIEGQPVEVLLDTGADDSIVT" is SEQ ID NO:25, "KGTIMT" is SEQ ID NO:26, and "TPINIFGRN-LLTAL" is SEQ ID NO:27. For the sequence ".TAHIEGQPVEVLLDTGADDSIVT . . . TKE . . . KIE . . . KGTIMI . . . TPINIFGRNLLTAL." named "d1tcwa_", "TAHIEGQPVEVLLDTGADDSIVT" is SEQ ID NO:28, "KGTIMI" is SEQ ID NO:29" and "TPINIFGRNLLTAL" is SEQ ID NO:30. For the sequence ".TAYIEGQPVEVLLDT-GADDSIVA . . . TKE . . . EIE . . . RATIMT . . . TPINIFGR-NILTAL." named "d1idaa_", "TAYIEGQPVEVLLDT-GADDSIVA" is SEQ ID NO:31, "RATIMT" is SEQ ID NO:32", and "TPINIFGRNILTAL" is SEQ ID NO:33. For the sequence ".TAYIEGQPVEVLLDTGADDSIVA . . . TLE . . . EIE . . . RATIMT . . . TPINIFGRNILTAL." named "d4upja_", "TAYIEGQPVEVLLDTGADDSIVA" is SEQ ID NO:34, "RATIMT" is SEQ ID NO:35, "TPINIFGRNILTAL" is SEQ ID NO:36. For sequence ".TIKIGGQLKEALLDT-GADDSIVA . . . VRQ . . . LIE . . . IGTVLV . . . TPINII-GRNIXTQI." named "d1bdqa_", "TIKIGGQLKEALLDT-GADDSIVA" is SEQ ID NO:37, "IGTVLV" is SEQ ID NO:38, "TPINIIGRNIXTQI" is SEQ ID NO:39. For sequence ".TIKIGGQLKEALLDTGADDSIVA . . . VRQ . . . LIE . . . IGTVLV . . . TPVNIIGRNLLTQI." named "d1bdla_", "TIKIGGQLKEALLDTGADDSIVA" is SEQ ID NO:40, "IGTVLV" is SEQ ID NO:41, "TPVNIIGRNLLTQI" is SEQ ID NO:42. For the sequence ".TIKIGGQLKEALLDTGAD-DTVIE . . . VRQ . . . IIE . . . IGTVLV . . . TPSNIIGRNLLTQI." named "d1klta_", "TIKIGGQLKEALLDTGADDTVIE" is SEQ ID NO:43, "IGTVLV" is SEQ ID NO:44, "TPSNII-GRNLLTQI" is SEQ ID NO:45. For the sequence ".TIKIG-GQLKEALLDTGADDTVLE . . . VRQ . . . LIE . . .

IGTVLV . . . TPVNIIGRNLLTQI." named "dlnh0a_", "TIKIGGQLKEALLDTGADDTVLE" is SEQ ID NO:46, "IGTVLV" is SEQ ID NO:47, "TPVNIIGRNLLTQI" is SEQ ID NO:48. For the sequence ".TIKIGGQLKEALLDTGADDTVIE . . . VRQ . . . IIE . . . IGTVLV . . . TPVNIIGRNLLTQI." named "dlq9pa_", "TIKIGGQLKEALLDTGADDTVIE" is SEQ ID NO:49, "IGTVLV" is SEQ ID NO:50, and "TPVNIIGRNLLTQI" is SEQ ID NO:51. For the sequence ".LIFVNGYPIKFLLDTGADITILN . . . GTN . . . HLE . . . FGNVCV . . . LIQPLLGRDNMIKF." named "D5fiva_", "LIFVNGYPIKFLLDTGADITILN" is SEQ ID NO:52, "FGNVCV" is SEQ ID NO:53, and "LIQPLLGRDNMIKF" is SEQ ID NO:54. For the sequence ".LIFVNGYPIKFLLDTGADITILN . . . GTN . . . HLE . . . FGNVCV . . . LIVPLLGRDNMIKF" named "d6fiva_" "LIFVNGYPIKFLLDTGADITILN" is SEQ ID NO:55, "FGNVCV" is SEQ ID NO:56, "LIVPLLGRDNMIKF" is SEQ ID NO:57. These spans were used to identify the residues with highest cScores in the protein structure of HIV-1 protease. Residue positions with high cScores (a sequence-based index in structure context, Zhou et al. 2005) are colored yellow. cScores were calculated using the functional alphabet and system of identity, non-identity and similarity described in the section above titled Similarity Metrics. These residues had the highest sequence and structure conservation in the cluster #1.

FIG. 7 illustrates the HIV-1 protease homodimer complexed with a dihydroethylene-containing inhibitor (PDB entry 1hiv chain A) as a reference protein upon which span residues with high cScores are projected. In FIG. 7, residues with a cutoff cScore percentile of 15% are colored in yellow. These high scoring residues were conserved among the retropepsins and also corresponded closely to the enzyme active site which binds the inhibitor (in grey). Adjusting, percentile cScore parameters made little difference in the detected residues. For example, only one residue, GLY(73) is not selected when more stringent parameters are applied (i.e., 10% percentile cScore cutoff). Conversely, only one additional residue is added to the set of highly conserve residues when the percentile cScore cutoff is lowered to 20%.

WORKING EXAMPLE 2

Tissue Plasminogen Activator

In a second working example, conservation of the protein structure of human trypsin IV (PDB entry: 1h4w) was characterized relative to a computationally identified family of protein structures. The characterized cScores for human trypsin IV were used to automatically detect a binding pocket in the human trypsin IV protein structure corresponding to a binding pocket in human tissue-type plasminogen activator (t-PA). These results agree with the previous observation (Lamba et al. 1996) that the pocket in catalytic domain of t-PA is almost identical to that of trypsin.

A local global structural alignment of the human trypsin IV protein structure and 207 protein structures from SCOP fold b.47, which represents the trypsin-like serine protease protein structures, was performed using LGA. FIG. 8 illustrates a local global structural alignment of 25 representative protein structures from SCOP fold b.47 using the protein structure of human trypsin IV as a reference protein structure. In FIG. 8, colored bars represent the Calpha-Calpha distance deviation between the superimposed protein structures and human trypsin IV protein structure (1h4w). Each bar represents protein structure residues from the N terminal (left) to the C terminal (right). Residue pairs superimposed with a distance below 2 Angstroms are colored green. Residues pairs superimposed with a distance below 4 Angstroms are colored in yellow. Residues superimposed below 6 Angstroms in orange, and residues at or above 6.0 Å in red. Terminal residues that were not aligned are colored in grey. Calculated global levels of sequence identity (Seq_ID) and structure similarity (LGA_S) between proteins from PDB and 1h4w are given in the right columns. The top 19 structures below the human trypsin IV protein structure in the bar diagram belong to the protein structure family b.47.1.2. The bottom 4 structures in the bar diagram belong to the b.47.1.4 and b.50.1.2 families. As evidenced by the alignment, structures in family b.47.1.2 had strong structural similarity with human trypsin IV.

FIG. 9 illustrates a clustering of the protein structure of human trypsin IV with 207 protein structures from the "b.47" family of protein structures in SCOP according to the STRALCP method outlined in FIG. 3. In the clustering, each of the 207 protein structures was computationally clustered into one of 6 clusters. For purposes of illustration, the dendogram only illustrates 4 clusters using 25 representative proteins. The human trypsin IV protein structure (shown as 1h4qw in the dendogram) clustered with human tissue-type plasminogen activator (t-PA; shown as 1rtfAB in the dendogram) and other proteins from SCOP family "b.47.1.2" in cluster #1. Cluster #1 corresponds to the black colored bar in FIG. 9.

The STRALCP algorithm was run with the following default parameters. Candidate spans of a minimum of 5 contiguous residues were identified from each pair-wise structural alignment using a pre-determined distance of 0.5 Angstroms for calculated root mean square deviations using a window size of 3 residues. Sequential fragments 10 residues in length were determined for each protein structure from fold a. 8. Pair-wise local similarity values indicating whether pairs of fragments shared candidate spans were calculated. An initial clustering was performed using a cutoff value of 80% non-empty fragments between each protein structure in each cluster. A second and final clustering was performed by applying a cutoff value of 60% global structure similarity to LGA_S scores generated for the pair-wise structural alignments.

FIG. 10 illustrates a multiple sequence structure alignment of cluster #1 showing the "spans" or locally aligned regions in cluster #1. Each row begins from the cluster number, followed by the domain name, and the set of amino-acids that are extracted from detected structurally conserved spans. Dots indicate regions that structurally deviate in at least one pair-wise comparison between members of the cluster. For purposes of illustration, only 19 of the 78 structures in cluster #1 are shown here). FIG. 10 lists the following sequences and SEQ ID NOs. For the sequence ".VM . . . GASLI.DRWV.TAAHC . . . LVRI . . . ISML . . . IYI . . . IALMKL . . . " named "ld6w_A", "GASLI" is SEQ ID NO:58, "DRWV" is SEQ ID NO:59, "TAAHC" is SEQ ID NO:60, "LVRI" is SEQ ID NO:61, "ISML" is SEQ ID NO:62, "IALMKL" is SEQ ID NO:63. For the sequence ".VS . . . GGSLI.EQWV.SAAHC . . . QVRL . . . FINA . . . IIR . . . IMLIKL . . . " named "1h4w_A", "GGSLI" is SEQ ID NO:64, "EQWV" is SEQ ID NO:65, "SAAHC" is SEQ ID NO:66, "QVRL" is SEQ ID NO:67, "FINA" is SEQ ID NO:68, "IMLIKL" is SEQ ID NO:69. For the sequence ".AA . . . GGILI.SCWI.SAAHC . . . TVIL . . . KFEV . . . YIV . . . IALLQL . . . " named "1rtfAB", "GGILI" is SEQ ID NO:70, "SCWI" is SEQ ID NO:71, "SAAHC' is SEQ ID NO:72, "TVIL" is SEQ ID NO:73, "KFEV" is SEQ ID NO:74", "IALLQL" is SEQ ID NO:75. For the sequence ".VS . . . GGSLI.SQWV.SAAHC . . . QVRL . . . FISA . . .

SIV ... IMLIKL ... " named "1ntp", "GGSLI" is SEQ ID NO:76, "SQWV" is SEQ ID NO:77, "SAAHC" is SEQ ID NO:78, "QVRL" is SEQ ID NO:79, "FISA' is SEQ ID NO:80, "IMLIKL" is SEQ ID NO:81. For the sequence ".VS ... GGSLI.SQWV.SAAHC ... QVRL ... FINA ... IIT ... IMLIKL ... " named "1fni_A", "GGSLI" is SEQ ID NO:82, "SQWV" is SEQ ID NO:83, "SAAHC" is SEQ ID NO:84, "QVRL" is SEQ ID NO:85, "FINA" is SEQ ID NO:86, "IMLIKL" is SEQ ID NO:87. For the sequence ".VS ... GGSLI.SQWV.SAAH ... QVRL ... FISA ... SIV ... IMLIKL ... " named "1v2n_T", "GGSLI" is SEQ ID NO:88, "SQWV" is SEQ ID NO:89, "SAAHC" is SEQ ID NO:90, "QVRL" is SEQ ID NO:91, "FISA" is SEQ ID NO:92, "IMLIKL" is SEQ ID NO:93. For the sequence ".VS ... GGSLI.DQWV.SAAHC ... QVRL ... FVNA ... IIT ... IMLIKL ... " named "1amh_A", "GGSLI" is SEQ ID NO:94, "DQWV" is SEQ ID NO:95, "SAAHC" is SEQ ID NO:96, "QVRL" is SEQ ID NO:97, "FVNA" is SEQ ID NO:98, "IMLIKL" is SEQ ID NO:99. For the sequence ".VS ... GGSLI.ENWV.SAAHC ... EVRL ... FISS ... VIR ... IMLIKL ... " named "1hj8_A", "GGSLI" is SEQ ID NO:100, "ENWV" is SEQ ID NO:101, "SAAHC" is SEQ ID NO:102, "EVRL" is SEQ ID NO:103, "FISS" is SEQ ID NO:104, "IMLIKL" is SEQ ID NO:105. For the sequence ".VA ... GGVLL.RNWV.TAAHC ... EVWL ... HRLV ... SFP ... LMLLRL ... " named "1ao5_A", "GGVLL" is SEQ ID NO:106, "RNWV" is SEQ ID NO:107, "TAAHC" is SEQ ID NO:108, "EVWL" is SEQ ID NO:109, "HRLV' is SEQ ID NO:110, "LMLLRL" is SEQ ID NO:111. For the sequence ".VS ... GGSLI.DQWV.SAAHC ... QVRL ... FVNA ... IIK ... IMLIKL" named "3tgj_E", "GGSLI" is SEQ ID NO:112, "DQWV" is SEQ ID NO:113, "SAAHC" is SEQ ID NO:114, "QVRL" is SEQ ID NO:115, "FVNA" is SEQ ID NO:116, "IMLIKL" is SEQ ID NO:117. For the sequence ".VS ... GGSLI.DQWV.SAAHC ... QVRL ... FVNA ... IIK ... IMLIKL ... " named "1esb", "GGTLI" is SEQ ID NO:118, "QNWV" is SEQ ID NO:119, "TAAHC" is SEQ ID NO:120, "RVVV" is SEQ ID NO:121, "YVGV" is SEQ ID NO:122, and "IALLRL" is SEQ ID NO:123. For the sequence ".AA ... GGSLI.PCWV.SATHC ... IVYL ... KFEV ... LIL ... IALLKI ... " named "1vja_U", "GGSLI" is SEQ ID NO:124, "PCWV" is SEQ ID NO:125, "SATHC" is SEQ ID NO:126, "IVYL" is SEQ ID NO:127, "KFEV" is SEQ ID NO:128, and "IALLKI" is SEQ ID NO:129. For the sequence ".VA ... GGTLI.PEWV.TAAHC ... QMQL ... TRNP ... KFI ... IMLIKL ... " named "1op0_A", "GGTLI" is SEQ ID NO:130, "PEWV" is SEQ ID NO:131, "TAAHC" is SEQ ID NO:132, "QMQL" is SEQ ID NO:133, "TRNP" is SEQ ID NO:134, and "IMLIKL" is SEQ ID NO:135. For the sequence ".AA ... GGSLM.PCWV.SATHC ... IVYL ... KFEV ... LIL ... IALLKI" named "1owe_A", "GGSLM" is SEQ ID NO:136, "PCWV' is SEQ ID NO:137, "SATHC" is SEQ ID NO:138, "IVYL" is SEQ ID NO:139, "KFEV" is SEQ ID NO:140, and "IALLKI" is SEQ ID NO:141. For the sequence ".AA ... GGSLM.PCWV.SATHC ... IVYL ... KFEV ... LIL ... IALLKI" named "1fv9_A", "GGSLM" is SEQ ID NO:142, "PCWV" is SEQ ID NO:143, "SATHC" is SEQ ID NO:144, "IVYL" is SEQ ID NO:145, "KFEV" is SEQ ID NO:146, and "IALLKI" is SEQ ID NO:147. For the sequence ".AA ... GGILI.SCWI.SAAHC ... TVIL ... KFEV ... YIV ... IALLQL" named "1bda_A", "GGILI" is SEQ ID NO:148, "SCWI" is SEQ ID NO:149, "SAAHC" is SEQ ID NO:150, "TVIL" is SEQ ID NO:151, "KFEV" is SEQ ID NO:152, and "IALLQL" is SEQ ID NO:153. For the sequence ".LS ... GASLL.STSA.SASHC ... RVIA ... TANV(SEQ ID NO:158) ... YTM ... IAILHL ... " named "1ij7_A", "GASLL" is SEQ ID NO:154, "STSA" is SEQ ID NO:155, "SASHC" is SEQ ID NO:156, "RVIA" is SEQ ID NO:157, "TANV" is SEQ ID NO:158, and "IAILHL" is SEQ ID NO:159. For the sequence ".VS ... GGSLI.PQWV.TAAHC ... RVQL ... LLPV ... IIV ... IALLEL ... " named "1a01_A", "GGSLI" is SEQ ID NO:160, "PQWV" is SEQ ID NO:161, "TAAHC" is SEQ ID NO:162, "RVQL" is SEQ ID NO:163, "LLPV" is SEQ ID NO:164, and "IALLEL" is SEQ ID NO:164). For the sequence ".AS ... GGALI.ARFV.TAASC ... TVVL ... TFSI ... MSE ... LMLLQL" named "lfy3_A", "GGALI" is SEQ ID NO:165, "ARFV" is SEQ ID NO:166, "TAASC" is SEQ ID NO:167, "TVVL" is SEQ ID NO:168, "TFSI' is SEQ ID NO:169, and "LMLLQL" is SEQ ID NO:170. These spans were used to identify the residues with highest cScores in the protein structure of human trypsin IV and tissue-type plasminogen activator (both marked in red). Residue positions with high cScores (a sequence-based index in structure context, Zhou et al. 2005) are colored yellow. cScores were calculated using the functional alphabet and system of identity, non-identity and similarity described in the section above titled Similarity Metrics. These residues had the highest sequence and structure conservation in the cluster #1.

Figure 11:
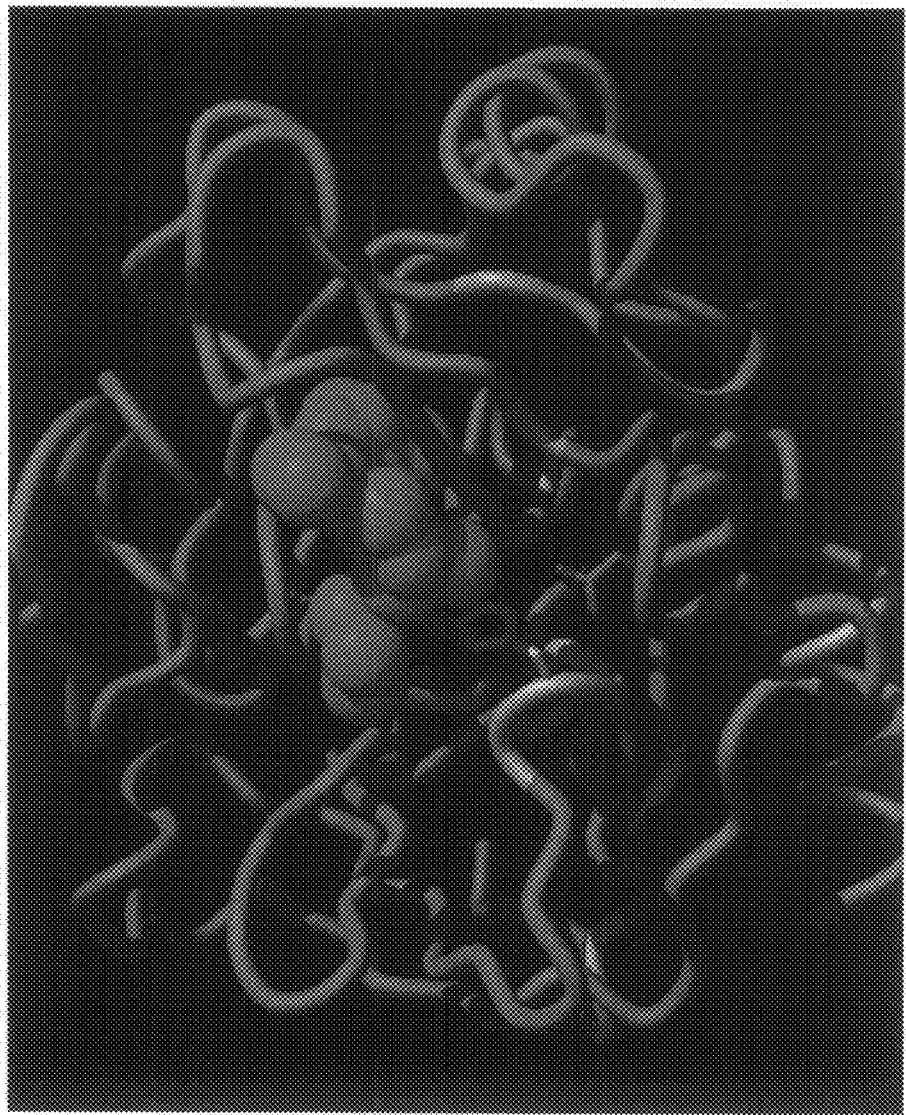
FIG. 11 illustrates a plot of the protein structure of human trypsin IV (1h4w) upon which span residues with high cScores are projected.

FIG. 11 illustrates a plot of the protein structure of human trypsin IV (1h4w) upon which span residues with high cScores are projected. In the plot span residues within high cScores in cluster #1 are colored in yellow. To the left of the yellow colored residues are a set of magenta spheres representing a binding pocket. This pocket was identified using UniquePocket software (Zhou et al. Bioinformatics 2005).

Figure 10:
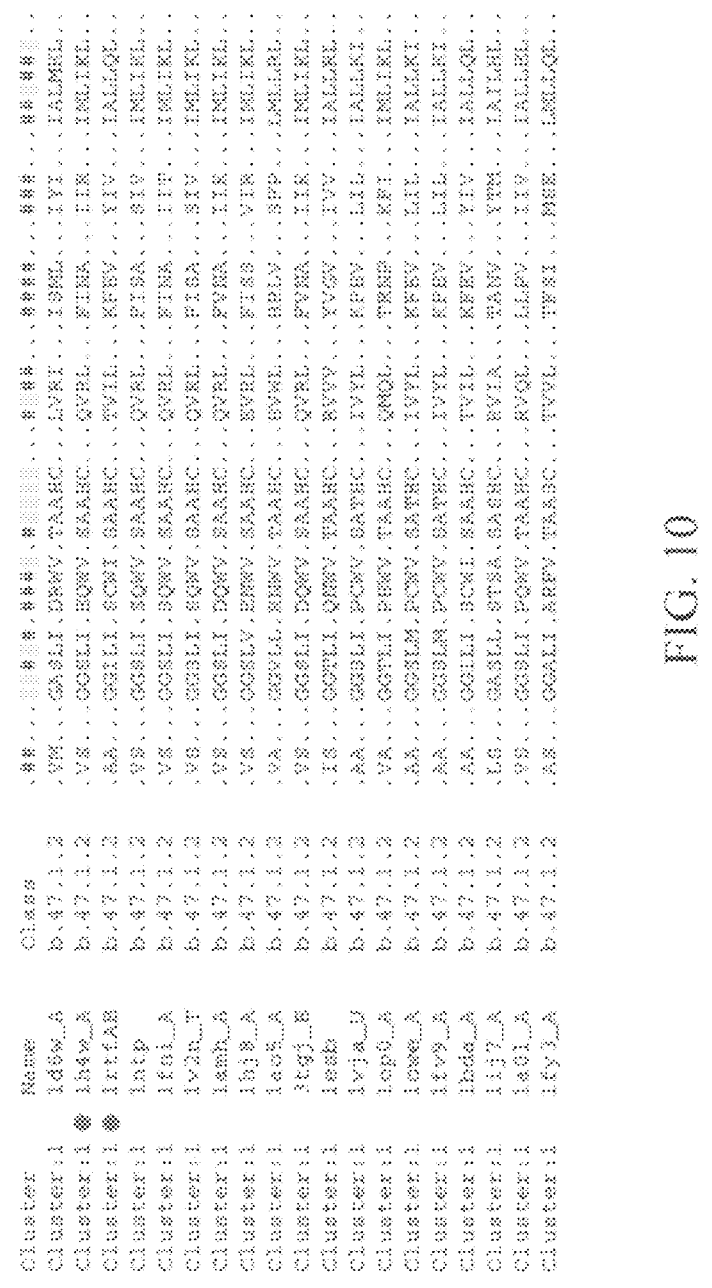
Figure 12:
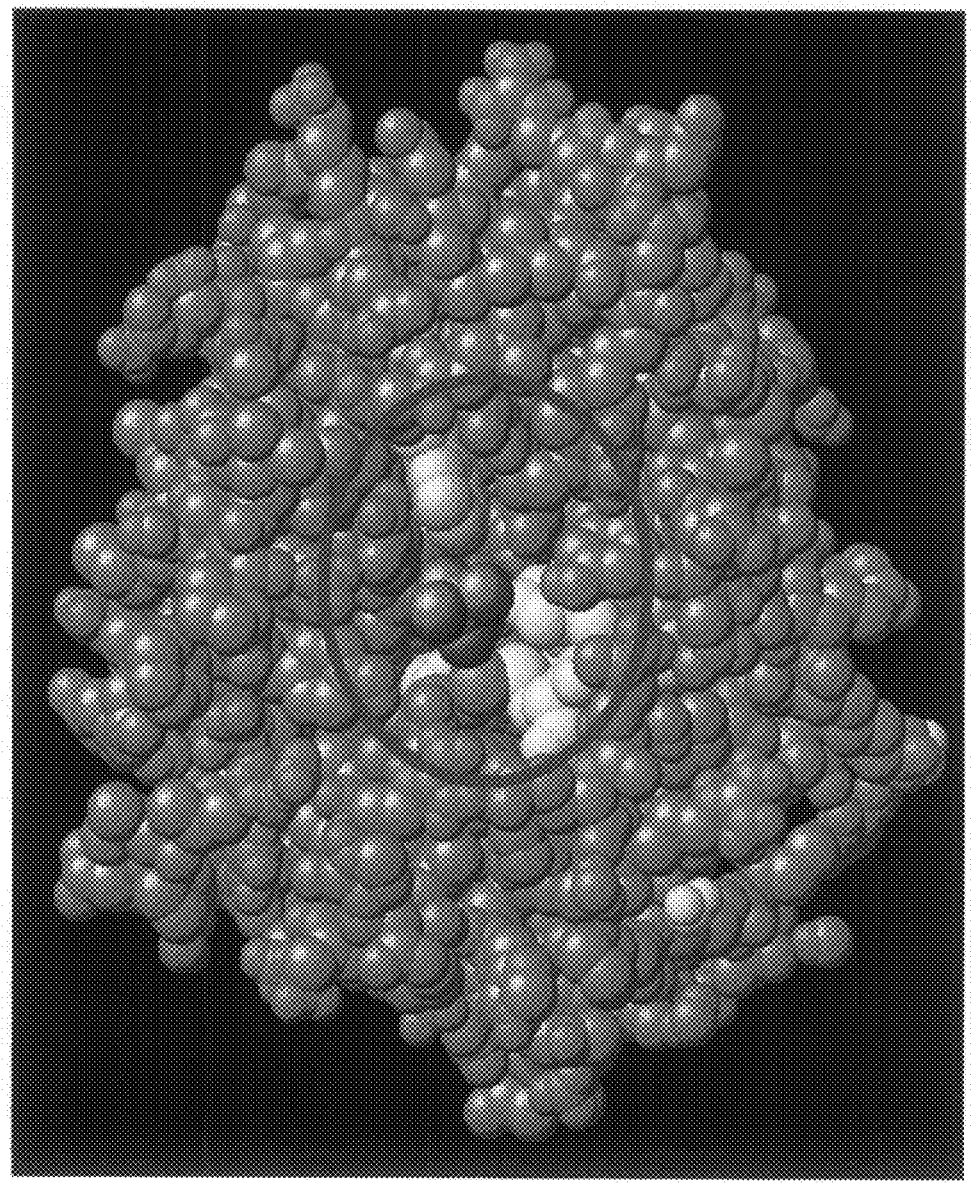
FIG. 12 illustrates a "spacefill" plot of the catalytic domain of human tissue-type plasminogen activator (t-PA; PDB entry: 1rtf) complexed with benzamidine (gray) and phosphate ion (red) upon which span residues with high cScores are projected.

FIG. 12 illustrates a "spacefill" plot of the catalytic domain of human tissue-type plasminogen activator (t-PA; PDB entry: 1rtf) complexed with benzamidine (gray) and phosphate ion (red). The circled area represents a binding pocket. Span residues with high in cluster #1 are colored in yellow and located in the bottom of the pocket. These high scoring residues correspond to those plotted in FIG. 10 and FIG. 11.

Reference in the specification to "one embodiment" or to "an embodiment" means that a particular feature, structure, or characteristic described in connection with the embodiments are included in at least one embodiment of the invention. The appearances of the phrase "in one embodiment" in various places in the specification are not necessarily all referring to the same embodiment.

Some portions of the above are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps (instructions) leading to a desired result. The steps are those requiring physical manipulations of physical quantities. Usually, though not necessarily, these quantities take the form of electrical, magnetic or optical signals capable of being stored, transferred, combined, compared and otherwise manipulated. It is convenient at times, principally for reasons of common usage, to refer to these signals as bits, values, elements, symbols, characters, terms, numbers, or the like. Furthermore, it is also convenient at times, to refer to certain arrangements of steps requiring physical manipulations of physical quantities as modules or code devices, without loss of generality.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or "determining" or the like, refer to the action and processes of a computer system, or similar electronic computing device, that manipulates and transforms data represented as physical (electronic) quantities within the computer system memories or registers or other such information storage, transmission or display devices.

Certain aspects of the present invention include process steps and instructions described herein in the form of an algorithm. It should be noted that the process steps and instructions of the present invention can be embodied in software, firmware or hardware, and when embodied in software, can be downloaded to reside on and be operated from different platforms used by a variety of operating systems.

The present invention also relates to an apparatus for performing the operations herein. This apparatus may be specially constructed for the required purposes, or it may comprise a general-purpose computer selectively activated or reconfigured by a computer program stored in the computer. Such a computer program may be stored in a computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

The algorithms and displays presented herein are not inherently related to any particular computer or other apparatus. Various general-purpose systems may also be used with programs in accordance with the teachings herein, or it may prove convenient to construct more specialized apparatus to perform the required method steps. The required structure for a variety of these systems will appear from the description below. In addition, the present invention is not described with reference to any particular programming language. It will be appreciated that a variety of programming languages may be used to implement the teachings of the present invention as described herein, and any references below to specific languages are provided for disclosure of enablement and best mode of the present invention.

While the invention has been particularly shown and described with reference to a preferred embodiment and several alternate embodiments, it will be understood by persons skilled in the relevant art that various changes in form and details can be made therein without departing from the spirit and scope of the invention.

Finally, it should be noted that the language used in the specification has been principally selected for readability and instructional purposes, and may not have been selected to delineate or circumscribe the inventive subject matter. Accordingly, the disclosure of the present invention is intended to be illustrative, but not limiting, of the scope of the invention, which is set forth in the following claims.

Protein Structure Modeling

Advances in protein structure prediction or modeling provide methods of computationally solving the set of atom coordinates for a given protein. According to the embodiment of the present invention, it may be necessary to generate a computationally solved or 'modeled' protein structure for one or more proteins identified for clustering, where the protein does not have an experimentally solved protein structure. The Sequence to Structure Module 210 functions to generate computationally solved protein structures based on three different techniques (sequence comparison, threading and ab initio modeling). The Sequence to Structure Module 210 typically generates computationally solved protein structure prediction using a combination of these techniques.

A favored method in the art of protein structure prediction is to find a close homolog for whom the structure is known. CASP (Critical Assessment of Techniques for Protein Structure Prediction) (Moult et al., 2003) experiments have shown that protein structure prediction methods based on homology search techniques are still the most reliable prediction methods. Sequence comparison and threading techniques are based on homology search.

Sequence comparison approaches to protein structure prediction are popular due to availability of protein sequence information. These techniques use conventional sequence search and alignment techniques such as BLAST or FASTA to assign protein fold to the query sequence based on sequence similarity.

Approaches which use protein profiles are similar to sequence-sequence comparisons. A protein profile is an n-by-20 substitution matrix where n is the number of residues for a given protein. The substitution matrix is calculated via a multiple sequence alignment of close homologs of the protein. These profiles may be searched directly against sequence or compared with each other using search and alignment techniques such as PSI-BLAST and HMMer.

It is known that sequence similarity is not necessary for structural similarity. Proteins sharing similar structure can have negligible sequence similarity. Convergent evolution can drive completely unrelated proteins to adopt the same fold. Accordingly, 'threading' methods of protein structure prediction were developed which use sequence to structure alignments. In threading methods, the structural environment around a residue could be translated into substitution preferences by summing the contact preferences of surrounding amino acids. Knowing the structure of a template, the contact preferences for the 20 amino acids in each position can be calculated and expressed in the form of a n-by-20 matrix. This profile has the same format as the position specific scoring profile used by sequence alignment methods, such as PSI-BLAST, and can be used to evaluate the fitness of a sequence to a structure.

Ab initio methods are aimed at finding the native structure of the protein by simulating the biological process of protein folding. These methods perform iterative conformational changes and estimate the corresponding changes in energy. Ab initio methods are complicated by inaccurate energy functions and the vast number of possible conformations a protein chain can adopt. The most successful approaches of ab initio modeling include lattice-based simulations of simplified protein models and methods building structures from fragments of proteins. Ab initio methods demand substantial computational resources and are also quite difficult to use, and expert knowledge is needed to translate the results into biologically meaningful results. Despite known limitations, Ab initio methods are increasingly applied in large-scale annotation projects, including fold assignments for small genomes. Recent examples of such applications include Bonneau et al. 2001, Kuhlman et al. 2003 and Dantas et al. 2003.

In practice, protein structure prediction typically involves a combination of the listed techniques, both experimental and computational. Hybrid approaches to protein structure prediction involve using different techniques for solving the atom coordinates at different stages or to solve for different parts of the protein structure. An example of this would be the use of AS2TS (amino acid to tertiary structure, a homology threading threading technique) to facilitate the molecular replacement (MR) phasing technique in experimental X-ray crystallographic determination of the protein structure of *Mycobacterium tuberculosis* (MTB) RmlC epimerase (Rv3465) from the strain H37rv. The AS2TS system was used to generate two homology models of this protein that were then successfully employed as MR targets.

Meta-predictors or consensus approaches attempt to benefit from the diversity of models by combining multiple techniques. In these methods, predictive models are collected and analyzed from a variety of different computational and experimental techniques. A common approach for combining models by consensus is to select the most abundant fold represented in the set of high scoring models. Other approaches to consensus modeling involve structural clustering such as HCPM-Hierarchical Clustering of Protein Models (Gront and Kolinski, 2005).

REFERENCES

Redfern, O., Grant, A., Maibaum, M., Orengo, C. (2005) Survey of current protein family databases and their application in comparative, structural and functional genomics. Journal Of Chromatography B-Analytical Technologies In The Biomedical And Life Sciences, 815 (1-2), 97-107.

Berman, H. M., Westbrook, J., Feng, Z., Gilliland, G., Bhat, T. N., Weissig, H., Shindyalov, I. N., and Bourne, P. E. (2000) The protein data bank. Nucleic Acids Research, 8, 235-242.

Murzin, A. G., Brenner, S. E., Hubbard, T., Chothia, C. (1995) SCOP: a structural classification of proteins database for the investigation of sequences and structures. J. Mol. Biol., 247, 536-540.

Orengo, C. A., Michie, A. D., Jones, S., Jones, D. T., Swindells, M. B., and Thornton, J. M. (1997) CATH—A Hierarchic Classification of Protein Domain Structures. Structure. Vol 5, No 8, 1093-1108.

Altschul, S. F., Madden, T. L., Scaffer, A. A., Zhang, J., Zhang, Z., Miller, W., Lipman, D. J. (1997) Gapped BLAST and PSI-BLAST: a new generation of protein database search programs. Nucleic Acids Research, 25, 3389-3402.

Ortiz, A. R., Strauss, C. E., Olmea, O. (2002) MAMMOTH (matching molecular models obtained from theory): an automated method for model comparison. Protein Sci, 11, 2606-2621.

Huan, J., Wang, W., Washington, A., Prins, J., Shah, R., and Tropsha, A. (2004) Accurate classification of protein structural families using coherent subgraph analysis. Pac. Symp. Biocomput. 411-422.

Zemla, A. (2003) LGA—A Method for Finding 3D Similarities in Protein Structures. Nucleic Acids Research, Vol. 31, No. 13, 3370-3374.

Geisbrecht, B. V., Hamaoka, B. Y., Perman, B., Zemla, A., Leahy, D. J. (2005) The crystal structures of EAP domains from *Staphylococcus aureus* reveal an unexpected homology to bacterial superantigens. Journal Of Biological Chemistry, 280 (17), 17243-17250.

Zemla, A., Ecale Zhou, C., Slezak, T., Kuczmarski, T., Rama, D. Torres, C., Sawicka, D., Barsky, D. (2005) AS2TS System for Protein Structure Modeling and Analysis. Nucleic Acids Research, 33, W111-W115.

Moult, J., Fidelis, K., Zemla, A. (2003) Hubbard T., Critical assessment of methods of protein structure prediction (CASP)-round V., Proteins.; 53 Suppl 6:334-9.

Dantas, G., Kuhlman, B., Callender, D., Wong, M. and Baker, D. (2003) A large scale test of computational protein design: folding and stability of nine completely redesigned globular proteins. J. Mol. Biol., 332, 449-460.

Hakansson, M., Petersson, K., Nilsson, H., Forsberg, G., Bjork, P., Antonsson, P., Svensson, L. A. (2000) The crystal structure of staphylococcal enterotoxin H: implications for binding properties to MHC class II and TcR molecules. J. Mol. Biol., 302, 527-537.

Al-Shangiti, A., Naylor, C., Nair, S., Briggs, D., Henderson, B., Chain, B. (2004) Structural Relationships and Cellular Tropism of Staphylococcal Superantigen-Like. Proteins Infect. Immun., 72, 4261-4270.

Arcus, V. L., Langley, R., Proft, T., Fraser, J. D., Baker, E. N. (2002) The three-dimensional structure of a superantigen-like protein, SET3, from a pathogenicity island of the *Staphylococcus aureus* genome. J. Biol. Chem., 277, 32274-32281.

Earhart, C. A., Mitchell, D. T., Murray, D. L., Pinheiro, D. M., Matsumura, M., Schlievert, P. M., Ohlendorf, D. H. (1998) Structures of five mutants of toxic shock syndrome toxin-1 with reduced biological activity. Biochemistry, 37, 7194-7202.

Prasad, G. S., Radhakrishnan, R., Mitchell, D. T., Earhart, C. A., Dinges, M. M., Cook, W. J., Schlievert, P. M., Ohlendorf, D. H. (1997) Refined structures of three crystal forms of toxic shock syndrome toxin-1 and of a tetramutant with reduced activity. Protein Sci., 6, 1220-1227.

Bonneau, R., Tsai, J., Ruczinski, I. and Baker, D. (2001) Functional inferences from blind ab initio protein structure predictions. J. Struct. Biol., 134, 186-190.

Kuhlman, B., Dantas, G., Ireton, G. C., Varani, G., Stoddard, B. L. and Baker, D. (2003) Design of a novel globular protein fold with atomic-level accuracy. Science, 302, 1364-1368. 61.

Bower, M. J., Cohen, F. E. and Dunbrack, R. L. (1997) Prediction of protein side-chain rotamers from a backbone-dependent rotamer library: a new homology modeling tool. J Mol Biol, 267, 1268-1282.

Canutescu A. A., Shelenkov A. A. and Dunbrack, R. L. (2003) A graph theory algorithm for protein side-chain prediction. Prot Sci, 12, 2001-2014.

Gront D., Kolinski A., HCPM—program for hierarchical clustering of protein models. Bioinformatics. July 15; 21(14):3179-80. Epub 2005 Apr. 19.

Zhou, C E, A Zemla, D Roe, M Young, M Lam, J S Schoeniger, and R Balhorn. 2005. Computational approaches for identification of conserved/unique binding pockets in the A chain of ricin. Bioinformatics 21:3085-3096

Karlin, S. and Ghandour, G. (1985) Multiple-alphabet amino acid sequence comparison of the immunoglobulin k-chain constant domain. Proc. Natl. Acad. Sci. USA, 82, 8597-8601.

Fygenson, D. K., Needlemen, D. J. and Sneppen, K. (2004) Variability-based sequence alignment identifies residues responsible for functional differences in a and b tubulin. Protein Science, 13, 25-31.

Lamba, D., Bauer, M., Huber, R., Fischer, S., Rudolph, R., Kohnert, U. & Bode, W. (1996). The 2.3 AÊ crystal structure of the catalytic domain of recombinant two-chain human tissue-type plasminogen activator. J. Mol. Biol. 258, 117±135.

What is claimed is:

1. A computer-implemented method of scoring a set of residues within a cluster of proteins from an initial set of three dimensional protein structures, comprising:
   identifying, by a computer, the initial set of three dimensional protein structures, each comprising a polypeptide sequence and structural coordinates;
   generating, by the computer, a plurality of pair-wise protein structure alignments of the set of three dimensional protein structures;
   for each pair of protein structures in the set:
      generating, by the computer, a first plurality of fragments from a first protein structure in the pair and a second plurality of fragments from a second protein structure in the pair, wherein each fragment is a polypeptide sequence of contiguous residues of a pre-determined length and has associated distances of structural coordinates of contiguous residue pairs;
      identifying, by the computer, a plurality of contiguous residue pairs from the first plurality of fragments and the second plurality of fragments having structural coordinates within the first pre-determined distance and having a pre-determined length, thereby identifying a plurality of pair-wise candidate spans for the pair;
      determining, by the computer, a pair-wise local similarity value that indicates the number of first plurality of fragments and second plurality of fragments that share candidate spans;
      determining, by the computer, a pair-wise global similarity value that indicates a number of residues that form a plurality of residue pairs from the first protein structure and the second protein structure, wherein a structural coordinate of each member of the residue pair falls within a second pre-determined distance based on the pair-wise structural alignment;
   generating, by the computer, a cluster of protein structures from the initial set of protein structures using the identified pair-wise candidate spans, the pair-wise local similarity values, and the pair-wise global similarity values;
   aligning, by the computer, all protein structures in the cluster to generate a one-to-one residue correspondence of the residue pairs for the cluster of protein structures;
   identifying, by the computer, a span from the cluster of protein structures, wherein each span comprises a set of one-to-one correspondences of residues that are within the first pre-determined distance of each other and within the second pre-determined distance based on the plurality of pair-wise structural alignments of the cluster of protein structures;
   generating, by the computer, a plurality of conservation scores for the cluster of protein structures, wherein the conservation scores are calculated for a plurality of residues within the span based on a metric for residue similarity; and
   storing, by the computer, the plurality of conservation scores, thereby scoring the set of residues within the cluster of protein structures.

2. The method of claim 1, wherein the first pre-determined distance is less than 0.5 Angstroms.

3. The method of claim 1, wherein the second pre-determined distance is less than 5.0 Angstroms.

4. The method of claim 1, wherein the span comprises 3 or more contiguous residues.

5. The method of claim 1, wherein 3 or more conservation scores are generated and stored.

6. The method of claim 5, further comprising selecting, by the computer, a subset of high-scoring residues based on the plurality of conservation scores.

7. The method of claim 1, further comprising displaying, by the computer, a first conservation score of the plurality of conservation scores with a representation of a selected protein structure of the cluster of protein structures.

8. The method of claim 7, wherein the representation is a three-dimensional representation of a selected protein structure of the cluster of protein structures.

9. The method of claim 7, wherein the representation is a representation of an alignment comprising the selected protein structure of the cluster of protein structures.

10. The method of claim 1, further comprising displaying, by the computer, said conservation scores with a linear representation of a selected protein structure of the cluster of protein structures.

11. The method of claim 1, wherein the plurality of protein structures comprises a structure obtained using x-ray crystallography, electron microscopy, nuclear magnetic resonance spectroscopy, computational protein structure modeling, or a combination thereof.

12. The method of claim 1, wherein the metric for residue similarity incorporates information about residue identity, residue non-identity and residue class, information defined by a substitution matrix or a combination thereof.

13. A computer-readable non-transitory storage medium comprising program code for scoring a set of residues within a cluster of proteins from an initial set of three dimensional protein structures, the program code comprising program code for:

identifying, by a computer, the initial set of three dimensional protein structures, each comprising a polypeptide sequence and structural coordinates;

generating, by the computer, a plurality of pair-wise protein structure alignments of the set of three dimensional protein structures;

for each pair of protein structures in the set:

generating, by the computer, a first plurality of fragments from a first protein structure in the pair and a second plurality of fragments from a second protein structure in the pair, wherein each fragment is a polypeptide sequence of contiguous residues of a pre-determined length and has associated distances of structural coordinates of contiguous residue pairs;

identifying, by the computer, a plurality of contiguous residue pairs from the first plurality of fragments and the second plurality of fragments having structural coordinates within the first pre-determined distance and having a pre-determined length, thereby identifying a plurality of pair-wise candidate spans for the pair;

determining, by the computer, a pair-wise local similarity value that indicates the number of first plurality of fragments and second plurality of fragments that share candidate spans;

determining, by the computer, a pair-wise global similarity value that indicates a number of residues that form a plurality of residue pairs from the first protein structure and the second protein structure, wherein a structural coordinate of each member of the residue pair falls within a second pre-determined distance based on the pair-wise structural alignment;

generating, by the computer, a cluster of protein structures from the initial set of protein structures using the identified pair-wise candidate spans, the pair-wise local similarity values, and the pair-wise global similarity values;

aligning, by the computer, all protein structures in the cluster to generate a one-to-one residue correspondence of the residue pairs for the cluster of protein structures;

identifying, by the computer, a span from the cluster of protein structures, wherein each span comprises a set of one-to-one correspondences of residues that are within the first pre-determined distance of each other and within the second pre-determined distance based on the plurality of pair-wise structural alignments of the cluster of protein structures;

generating, by the computer, a plurality of conservation scores for the cluster of protein structures, wherein the conservation scores are calculated for a plurality of residues within the span based on a metric for residue similarity; and storing, by the computer, the plurality of conservation scores, thereby scoring the set of residues within the cluster of protein structures.

14. The computer-readable storage medium of claim 13, further comprising displaying a first conservation score of the plurality of conservation scores with a representation of a selected protein structure of the cluster of protein structures.

15. The computer-readable storage medium of claim 13, wherein the metric for residue similarity incorporates information about residue identity, residue non-identity and residue class, information defined by a substitution matrix or a combination thereof.

* * * * *